US012578305B2

(12) United States Patent
Dwyer et al.

(10) Patent No.: US 12,578,305 B2
(45) Date of Patent: Mar. 17, 2026

(54) PHOTOSWITCHABLE BINARY NANOPORE CAPABLE OF DETECTING SINGLE MOLECULES

(71) Applicants: University of Rhode Island Board of Trustees, Kingston, RI (US); Brandeis University, Waltham, MA (US)

(72) Inventors: Jason R Dwyer, Providence, RI (US); James Hagan, West Warwick, RI (US); Grace G.D. Han, Belmont, MA (US); Alejandra Gonzalez, Waltham, MA (US)

(73) Assignees: University of Rhode Island Board of Trustees, Kingston, RI (US); Brandeis University, Waltham, MA (US)

( * ) Notice: Subject to any disclaimer, the term of this patent is extended or adjusted under 35 U.S.C. 154(b) by 360 days.

(21) Appl. No.: 18/121,505

(22) Filed: Mar. 14, 2023

(65) Prior Publication Data

US 2023/0384261 A1 Nov. 30, 2023

Related U.S. Application Data

(60) Provisional application No. 63/332,692, filed on Apr. 20, 2022.

(51) Int. Cl.
*G01N 27/447* (2006.01)
*B82Y 15/00* (2011.01)
*G01N 33/487* (2006.01)

(52) U.S. Cl.
CPC ........ *G01N 27/44791* (2013.01); *B82Y 15/00* (2013.01); *G01N 33/48721* (2013.01)

(58) Field of Classification Search
None
See application file for complete search history.

(56) References Cited

U.S. PATENT DOCUMENTS 10,613,076 B2 4/2020 Meller

FOREIGN PATENT DOCUMENTS

EP 3771687 A1 2/2021

OTHER PUBLICATIONS

N. Di Fiori, et al., "Optoelectronic control of surface charge and translocation dynamics in solid-state nanopores", Nature nanotechnology, 8: p. 946-951, Dec. 2013.*
N. Liu, et al., "Photoregulation of Mass Transport through a Photoresponsive Azobenzene-Modified Nanoporous Membrane", Nano Letters, 4(4): p. 551-554, Apr. 2004.*
Chandramouli, B. et al. "Introducing an artificial photo-switch inot a biological pore: A model study . . . " Biochimica et Biophysica Acta 1858 (2016) 689-697.
Chambers, J. et al. "Light-Activated Ion Channels for Remote Control of Neural Activity" Methods Cell Biol. (2008) 90: 217-232.

(Continued)

*Primary Examiner* — J. Christopher Ball
(74) *Attorney, Agent, or Firm* — Milstein Zhang & Wu LLC; Duan Wu, Esq.

(57) ABSTRACT

Disclosed herein is the fabrication of a photo-regulated nanopore by covalently linking a photoswitch to the interior of a silicon-based membrane and related methods of translocating an analyte and distinguishing molecule types through such a nanopore.

24 Claims, 17 Drawing Sheets
(16 of 17 Drawing Sheet(s) Filed in Color)

(56) References Cited

OTHER PUBLICATIONS

Zelenak, V. et al., "Photo-switchable nanoporous silica supports for controlled drug delivery," New J. Chem., (2018) 42, 13263-13271.
Vlassiouk, I. et al., in "Control of Nanopore Wetting by a Photochromic Spiropyran—a Light-Controlled Valve and Electrical Switch," Nano Lett. (2006), 6(5), 1013-1017.
Ma, T. et al., "Combining Light-Gated and pH-Responsive Nanopore Based on PEG-Spiropyran Functionalization," Adv. Mater. Interfaces, (2018), 5, 1701051.
Laucirica, G. et al., "Redox-Driven Reversible Gating of Solid-State Nanochannels," ACS Appl. Mater. Interfaces, (2019) 11, 30001-30009.
Li, P. et al., "Light-Driven ATP Transmembrane Transport Controlled by DNA," Nanomachines. J. Am. Chem. Soc. (2018) 140, 16048-16052.

* cited by examiner

FIG. 2A
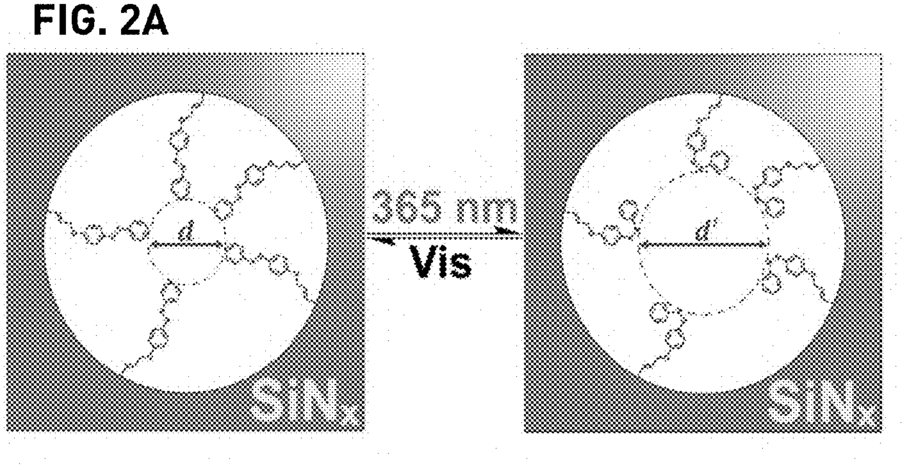
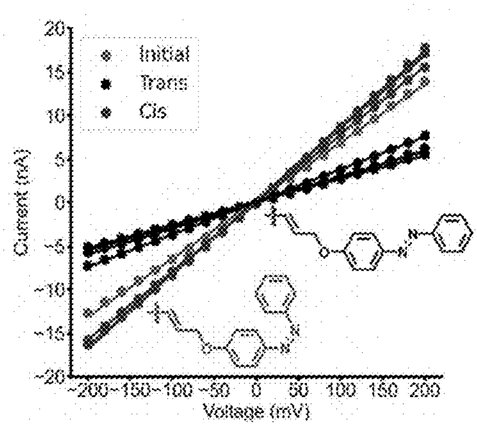
FIG. 2B
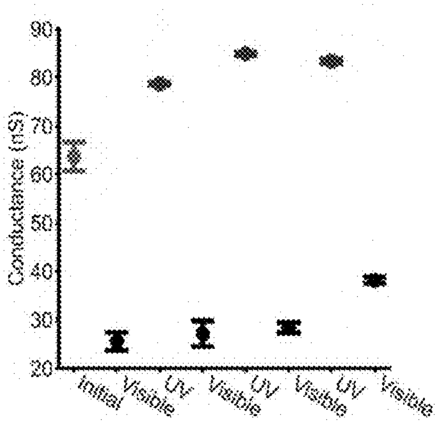
FIG. 2C

PHOTOSWITCHABLE BINARY NANOPORE CAPABLE OF DETECTING SINGLE MOLECULES

CROSS-REFERENCE TO RELATED APPLICATIONS

This application claims priority to, and the benefit of, U.S. Provisional Application 63/332,692, "Photoswitchable Binary Nanopore Conductance and Selective Electronic Detection of Single Biopolymers Under Wavelength and Voltage Polarity Control," filed Apr. 20, 2022, which is incorporated herein by reference in its entirety.

STATEMENT REGARDING FEDERALLY SPONSORED RESEARCH OR DEVELOPMENT

This invention was made with government support under grant number HG011096 awarded by the National Institutes of Health and grant number 1808344 awarded by the National Science Foundation. The government has certain rights in the invention.

STATEMENT REGARDING PARTIES TO A JOINT RESEARCH AGREEMENT

The University of Rhode Island Board of Trustees and Brandeis University were subject to a joint research agreement effective on or before the effective date of the claimed invention.

BACKGROUND OF THE INVENTION

Solid-state abiotic nanopores capture the imagination and have emerged in applications as high-performance platforms for single-molecule science, as nanoscale apertures for fundamental physics experiments and controlled cargo delivery, as conductive and often rectifying ionic circuit elements, as high-resolution model systems for nanoporous filters and as robust, device-ready analogues and mimics of their proteinaceous brethren.

Known in the art are various photocontrollable nanopores based on biological or similar membranes. The Rijksuniversiteit Groningen and the Academisch Ziekenhuis Groningen (NL) describe photo-controlled analyte sensing in "Reversible photo-controlled frac nanopores, modified frac monomers, methods for preparing the same, and uses thereof" (EP 3,771,687 A1). In this work, single pores can be created by allowing a toxin modified to include a photo responsive tail which can penetrate a bilayer to attach to a cell and is then irradiated. The photochromic switching in this work does not affect the properties or dimensions of a pore, but only controls whether a pore is opened or not, grossly modulating the overall porosity of the cell without any selectivity as to which molecules are transported—so the control offered is limited to increasing the susceptibility of cells to penetration of externally present chemicals, such as a cancer treatment compound. There is no selectivity for potential sensing applications, and the technique only applies to biotic or pseudo-biotic lipid membranes. Note that the structure created in this work penetrates through a membrane and does not control any interior pore properties or provide a functional coating which could be used to control a more robust abiotic pore.

A means for adding an externally attached photo-controlled switch atop a cell pore is described by Chandramouli, et al., in "Introducing an artificial photo-switch into a biological pore: A model study of an engineered α-hemolysin." Biochimica et Biophysica Acta, 2016, 1858, 689-697. In as much as the switch is external to the pore it cannot, by definition, control pore dimensions or any nano-scale properties of the biological pore. While still nanoscale, the control in this work is limited to relatively crude steric effects based on overall molecular configurations to block or unblock the biotic pore—and is suited only to control overall flux across the cell membrane. Despite the title of this work, the switch is not actually introduced in the pore, but rather laid on top of the pore. Further, the switch here is based on single molecules and thus cannot benefit from cooperative effects from a population of local functionalized molecules. Also, the structure itself is also delicate and susceptible to decomposition, severely limiting potential filtering or analytical applications. Moreover, the approach here only works for a very small size range of molecules and accordingly, the authors cannot use any interaction within the pore itself to sense molecules passing through the pore or providing specific control of any molecules passing through.

In what might be a more robust approach providing similar non-specific pore control, J. J. Chambers & R. H. Kramer in "Light-Activated Ion Channels for Remote Control of Neural Activity," Methods Cell Biol. 2008, 90, 217-232, modify the end of a channel protein with an azobenzene to create a photo modulated pore having similar limitations as in the work by Chandramouli, et al., such as very limited size range and no specific control for any osmotic or active molecular transport across the membrane.

Also known in the art are pores, unlike the foregoing biotic or similar membranes, that are created in connection with abiotic substrates. An example is found in V. Zelenak, et al., "Photo-switchable nanoporous silica supports for controlled drug delivery," New J. Chem., 2018, 42, 13263-13271. This paper describes the use of multiple coumarin molecules which are applied to the outside of a silica micropore wherein the coumarin molecules are driven to form a dimer using visible light. The dimerized coumarin traps a molecule of interest within the pore which can be released by irradiating the pore with ultraviolet (UV) light. However, such a dimeric system can only function for a small range of pore sizes having a characteristic size compatible with the employed dimers, and the dimer system described is said to function only on the exterior surface of the silicon pore.

Unlike much of the work above involving molecular configuration of reactions, pore control in planar SiN substrates is described by Meller et al. ("Optoelectronic control of solid-state nanopores," U.S. Pat. No. 10,613,076 B2, issued Apr. 7, 2020). Meller et al. aim to achieve pore control though purely optoelectronic means by manipulating the surface charges in the pore via light supplied by a laser, and they claim to be able to characterize an analyte by controlling the translocation speed of biopolymers, such as DNA, through these SiN pores.

I. Vlassiouk et al., in "Control of Nanopore Wetting by a Photochromic Spiropyran—a Light-Controlled Valve and Electrical Switch," Nano Lett. 2006, 6(5), 1013-1017, claim to gate the entry of water into a pore by altering the hydrophobicity of spiropyran believed to be located on the surface of an alumina membrane. Vlassiouk et al. claim that the relevant structure acts as a "burst valve" providing a two-order-of-magnitude change in the flow of ionic or non-ionic fluids. When used with an ionic fluid, the device can function as a switch. Note that this work does not address the important issues of molecular sensitivity or uses related to biomolecules. In as much as nanopores in alumina are long compared to those in SiNx materials, the paper suggests that the photoisomerization leaves the nanopore in a state where the energy barrier to dewetting interferes with switching, meaning that, after being "burst" open to allow entry of an aqueous liquid, Vlassiouk et al. were unable to switch the pore off.

T. Ma et al., in "Combining Light-Gated and pH-Responsive Nanopore Based on PEG-Spiropyran Functionalization," Adv. Mater. Interfaces, 2018, 5, 1701051, describe the construction of relatively long pores whose interior surface has been functionalized by attaching a PEG molecule to a spiropyran bound to the pore interior. The Spiropyran provides light sensitivity, and the PEG provides a response to pH conditions. By varying the Spiropyran configuration and the pH, the pore can be selective for anions under acidic conditions, and for cations at a neutral pH. Thus, the pores could function as rectifying circuit components. However, there is no suggestion that Ma et al.'s devices can support a driven biomolecular transport, let alone providing selectivity over the process.

G. Laucirica et al., in "Redox-Driven Reversible Gating of Solid-State Nanochannels," ACS Appl. Mater. Interfaces, 2019, 11, 30001-30009, show how a redox-sensitive coating external to a pore in a PET membrane can be used to control iontronic behavior at the entrance to a pore. Function in this device is related to the coating's electrostatic charge suitable for the control of non-specific ion species. The approach is not susceptible to selectivity based on polarity or steric differences in analytes.

Remarkably different from the foregoing, though related to transport through membranes, P. Li et al., in "Light-Driven ATP Transmembrane Transport Controlled by DNA," Nanomachines. J. Am. Chem. Soc. 2018, 140, pp. 16048-16052, describe how a binding transport molecule can be driven by alternating light frequencies to periodically transport ATP molecules across a membrane. This work shows how molecular motors can be used to move molecules across a membrane, in contrast to the present disclosure which concerns electrophoretic and electro-osmotic flow.

In most undertakings based on abiotic nanopores, a nanopore is immersed in an ionic electrolyte with the ~10 nm-diameter channel providing the only path for mass transport driven by a current along the ~10 nm channel length. For example, in the application of single-molecule DNA sequencing, electrophoresis of a DNA strand through a nanopore alters the ionic current flow to give rise to characteristic signals that can be used to recover the DNA base sequence.

Photo-responsive nanopores are even more appealing than already compelling conventional pores. Nonlocal, non-contact, and wavelength-selectable control of photo-responsive nanopores can significantly enhance their properties and capabilities. Molecular photoswitches that respond to light by configurational changes are a prominent tool that can, when suitably coupled to a nanopore, be used to optically control aspects of its nanoscale structure and function. Photoswitches including spiropyrans, hydrazones, donor-acceptor Stenhouse adducts, stilbenes, and azobenzenes isomerize upon light irradiation that leads to changes in their structure, polarity and various electrical and photophysical properties. Such molecular-scale changes to the coating can have longer-range effects including altering interfacial properties, e.g., the Debye-layer, that in turn control dynamic processes like nanoscale mass transport through the nanopore. Molecular-scale changes to the nanopore coating can thus modulate the sensing of ions, small and macromolecules, and nanoparticles and viruses.

Photo-switchable nanopores using a robust and adaptable nanopore platform suitable for a wide range of downstream applications have been investigated. Low-pressure chemical vapor deposition (LPCVD) silicon-rich silicon nitride ($SiN_x$) is the most prevalent and conventionally versatile nanopore fabrication material. It is a standard material in microelectronics so that the integration of nanopores into complex devices can be conceived of alongside manufacturing at-scale. Azobenzenes, in particular, display facile switching with alternating UV and visible light irradiation between the ground-state trans isomeric form and the metastable counterpart, cis isomer. The cis-to-trans reverse isomerization can be also promoted by thermal activation, offering an additional method of switching. However, further improvements including much needed stability and versatility in photoswitchable nanopores have not been seen in the art.

BRIEF SUMMARY OF THE DISCLOSURE

The present disclosure is directed to the fabrication and use of a photo-regulated thin-film nanopore sensor with improved stability, the ability to switch on-and off for different molecule types, low signal noise, and the capability to be reconfigured to sense different molecule types or analytes in a sample. In general, the photo-regulated thin-film nanopore sensor is fabricated by covalently linking azobenzene photoswitches to the interior of a silicon nitride pore.

Generally, an azobenzene has the following formula:

(Formula 1)

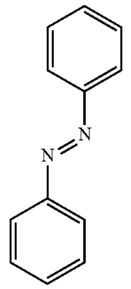

Generic Azobenzene

According to the present invention, a photo-responsive monolayer is provided on the internal wall surface of an abiotic nanopore, repeatedly and optically switchable with deterministic changes to the effective physical diameter and modulation from responsiveness to non-responsiveness in terms of sensing single molecules, e.g., biopolymers, whether charged or largely neutral. For example, embodiments of the present invention can be used to sense biopolymers such as oligo- or polynucleotides, oligo- or polypeptides, and oligo- or polysaccharides, natural or manmade. In an exemplary embodiment of the present invention, systems and methods are provided for sensing DNA and a complex carbohydrate, or to distinguish between the two within a sample.

Such controllable switching can be important for the use of nanopores as ionic circuit elements such as binary bits, filters, nanoscale confined chemical reactors, and as a platform for studying and harnessing stimuli-responsive mass transport. The demonstrated ability to tune the nanopore sensitivity by irradiating the pore surface with light of differing wavelengths and changing voltage levels and/or polarities to discriminate between nucleic acid and carbohydrate biopolymers is important for genomics and glycomics research and downstream applications such as personalized medicine and biopolymer information storage schemes. The two analyte classes also provide physicochemical diversity—beyond their charged (DNA) and neutral (polysaccharides, e.g., maltodextrin) nature—that is useful for fundamental studies of mass transport to probe and challenge the photochromic pore and for the potential to multiplex biopolymer data storage. The present invention fulfills the need for repeatably photo-controlled and stable features in terms of nanopore size, polarity, conductance, and sensing selectivity—conveniently provided without mass flow in a sealed cell by illumination wavelength and voltage polarity. Such a device is useful for a host of studies and applications, including those with single-molecule sensing of biologically important molecules. Configurations allowing net mass flow also have a range of applications. The novel photo-regulated nanopore sensors of the instant application exhibit the desired characteristics.

A photo-isomerizable compound (e.g., an azobenzene or azobenzene derivative) covalently coupled to the interior wall surface of a thin-film nanopore and remaining photo-switchable is provided herein to effectively control the size, cross-membrane conductance and polarity of nanopore systems. A stable monolayer with configurations resulting in effective physical nanopore diameter, conductance and polarity was achieved. This optical control enhanced nanopore single-molecule sensing. The azobenzene-festooned nanopores were tested with different classes of analytes—polynucleotides and polysaccharides. Each presented different physicochemical properties to the nanopore, and each was drawn from a molecular class core for pursuits within genomics and glycomics, respectively, and which are sufficiently diverse as to demonstrate operation underlying a range of molecular scale applications.

In an aspect, the invention provides a re-configurable translocation device capable of selectively translocating molecular types within a sample solution or translocating both the sample solution and molecular types, and distinguishing those molecule types contained therein, the device comprising a cell that includes:

(a) a source reservoir capable of holding a source solution and configured to be in electrical communication with an electrical source outside the cell, (b) a target reservoir capable of holding a target solution and configured to be in electrical communication with the electrical source outside the cell, and (c) a silicon-based membrane disposed between the source reservoir and the target reservoir, the membrane having at least one interior surface defining a nanopore having an average diameter between about 1 nm and about 100 nm, where the nanopore fully penetrates the membrane allowing passage of molecules between the source reservoir and the target reservoir, and where the interior surface defining the nanopore has been functionalized with at least one functional group comprising a photo-isomerizable compound. Further, the photo-isomerizable on the nanopore surface is responsive to either visible or ultraviolet light or both (or thermal energy) with at least one configurational change that alters the steric size of the photo-isomerizable compound and effects distinguishing one molecule type from another based on a detectable change in electroosmotic or electrophoretic transport of the sample, thereby re-configures the nanopore, and where the detectable change comprises a change in pore conductance in connection with the passage of a molecule type through the nanopore; and where, when an electrical potential is applied between the electrical source outside the cell and both the source reservoir and the target reservoir, measurements of electrical signals, e.g., pulses corresponding to electrical resistance changes, between the source reservoir and the target reservoir can be made, thereby providing distinguishing information on different molecule types that pass between the source reservoir and the target reservoir.

In another aspect, the invention provides a method of separating molecule types in a source solution using a re-configurable translocation device of the invention, e.g., based on a cell employing a nanopore similar to that in FIG. 1A, by optionally configuring the nanopore using visible or ultra-violet light to set an initial specificity for a molecular type, then applying an electrical potential across the cell for long enough to selectively translocate a molecular type from the source reservoir into a target reservoir while preventing the translocated molecular type from passing back into the source reservoir—typically by operating a valve before removing the electrical potential. The separated molecular type can be removed for whatever use desired. Next, the nanopore can be re-configured by subjecting the nanopore surface and the coated functional group which contains the photo-isomerizable compound to radiation of visible or ultra-violet light, or thermal energy (or by otherwise changing the nanopore conductance, voltage polarity applied, the charge distribution or characteristics of the pore surface, hydrophilicity of the pore surface, ionic-solvent-concentration, or ionic-solvent-pH value) and then re-applying an electrical potential, possibly of both a different polarity and voltage, across the cell. As before, the cell can then be operated for a sufficient time to translocate a different molecular type into the target reservoir.

In one feature, the foregoing method can be enhanced through the addition of a chemical which promotes a change in any of the properties used to re-configure the nanopore which can alter the selectivity of the nanopore to one or more molecular types.

In a further feature of the foregoing method, the solvent in the cell may be changed to optimize nanopore re-configuration, such as by switching between an organic solvent and aqueous solvent, prior to applying the electrical potential.

In a variation of the above method, a polar solvent, such as acetonitrile can be added to a generally non-polar organic solvent in the process of re-configuring the nanopore prior to applying the electrical potential.

In a particular application of the invention, distinguishing between two molecule types in an ionic fluid can be achieved, preferably with high specificity, by altering the ratio or direction of electroosmotic transport to electrophoretic transport through the nanopore such that different molecular types are selectively transported. This technique can distinguish between molecule types that do not differ in steric (or other) properties such that sieves (or other means) would be ineffective.

In a feature of an apparatus that can be used to practice the invention, a nanopore fully penetrates a membrane which can be made from a range of materials such as a polymer (e.g., those derived from petroleum and used to make a plastic), an MXene, a transition metal dichalcogenide, silicon, silicon oxide, silicon nitride, molybdenum disulfide or hexagonal boron nitride.

In another feature of an apparatus that can be used to practice the invention, a covalently bonded monolayer coats a substantial percentage, for example, 10%, 25%, 35%, 45%, 50% 60%, 75%, 85%, 90% or 100% of the surface of the nanopore. The thickness of said monolayer is preferably between 0.1 nm and 25 nm±5% or less, and the diameter of the pore can be changed by a factor between 0 and approximately twice the length of a fully extended photoswitched molecule when that molecule is changed between its available photo-isomers.

In a feature of the invention, the translocation device can alternatively be re-configured to distinguish between molecular types in either a closed configuration (with no net mass flow in or out), or in an open configuration suitable for processing pre-determined volumes of sample solutions.

In another feature of the invention, multiple nanopores, either carefully tailored to be of similar sizes, or tailored to be of varying sizes in a controlled range, can be incorporated in the membrane in cell according to the invention. Multiple nanopores allow improvements in the number of molecules that can be translocated though the device in a given unit of time, and provide an opportunity to modulate selectivity for molecular types having a range of properties.

In yet another feature of the invention, highly stable pore behavior can be realized, and that stability can be preserved by, among other things, limiting the nanopore pore-voltage gradient and exposure to light, and controlling the pH range and solvent to maintain the uniformity of the functionalized interior surface. In this aspect, the invention provides a translocation device where etching of a nanopore is minimized and clogging of a nanopore during operation is likely minimized.

In even another feature of the invention, selective responsivity can be achieved with regard to important classes of molecule types such as oligo- and polynucleotides (DNA, RNA, etc.), oligo- and polypeptides (proteins), oligo- and polysaccharides (for example, maltodextrin), and other carbohydrates, and mixtures thereof, in a manner where these molecule types can reliably be differentiated from each other. Moreover, the translocation device can employ a range of photoswitchable, photochromic molecules such as spiropyrans, hydrazones, donor-acceptor Stenhouse adducts, stilbenes, azobenzene, azobenzene derivatives, diarylethenes and diarylethene derivatives and dithienylethenes and dithienylethene derivatives.

The foregoing selective responsivity can provide discrimination between molecular types that are either neutral or charged and combinations thereof.

In an exemplary embodiment, the invention provides the ability to tune the nanopore from being responsive to being nonresponsive relative to sensing DNA, a complex carbohydrate or other biopolymers (e.g., oligo- or polynucleotides, oligo- or polypeptides, oligo- or polysaccharides), other polymers, small molecules and mixtures thereof. In a specific embodiment where the sample containing both a DNA molecule and a neutrally charged, complex carbohydrate (e.g., maltodextrin), the device of the invention is first configured, via optical or thermal radiation, to tune the photo-isomerizable functional group coating the interior wall of the nanopore, e.g., an azobenzene or azobenzene derivative, to be in a cis-configuration. Then the polarity of the voltage across the nanopore is set to allow selection of which specific analyte to pass through and thereafter isolated.

In a related aspect of the invention, photo-regulated nanopore sensors can then be manufactured using a process such as dielectric breakdown, ion bombardment, electron-milling, helium ion milling, or focused ion beam (FIB) milling of a membrane to first produce pores with an average diameter between about 1 nm and about 100 nm. The pores can then be functionalized by, for example, using photohydrosilyation of an azobenzene to a silicon nitride membrane until, for example, 4-(propargyloxy)azobenzene forms a monolayer covering a substantial portion, i.e., at least 10%, 25%, 50%, 75%, 90% or 100% of the pore surface. Preferably, the thickness of a silicon nitride membrane manufactured in this manner is in a range defined with a tolerance such as ±5% in a thickness between 1 to 100 nm.

BRIEF DESCRIPTION OF FIGURES

The patent or application file contains at least one drawing executed in color. Copies of this patent or patent application publication with color drawings will be provided by the Office upon request and payment of the necessary fee. The present disclosure may be better understood with reference to the following figures.

FIG. 2A, FIG. 2B, and FIG. 2C illustrate the initial conductance of the nanopore before light irradiation was measured. FIG. 2A illustrates the azo-switch coated pore when placed alternately under a UV flashlight (365 nm) and white light source to convert the azobenzene from its trans to cis configurations, and vice versa, respectively. FIGS. 2B, and 2C plot the measurements of the conductance after each step of photoirradiation. The physical changes in monolayer effective thickness—illustrated by the dashed circle—generated statistically significant changes in conductance, making the nanopore an effective switch.

In FIG. 8B, aliquots of the originally all-trans azo-benzene material were collected at intervals from a solution otherwise continuously irradiated in a quartz cuvette using the mercury UV lamp. No decomposition products of this molecule were detected, but an overall conversion from a purely trans to a mixed cis/trans sample in bulk solution was evident.

In FIG. 11A, it took about 15 minutes for the cis isomer to reach the photostationary state under 365 nm irradiation and about 90 minutes to reach the trans photostationary state with white light irradiation. In FIG. 11B, it took about 15 minutes for the cis isomer to reach the photostationary state under 365 nm irradiation, and about 90 minutes to reach the trans photostationary state under white light irradiation. In FIG. 11C, it took about 10 minutes for the cis isomer to reach the photostationary state under 365 nm irradiation, and about 85 minutes for the cis compound to thermally revert to the trans isomer upon heating at 75° C. The trans isomer was soluble in the aqueous solution at the high temperature and precipitated upon cooling to 25° C.

DETAILED DESCRIPTION

Figure 1A:
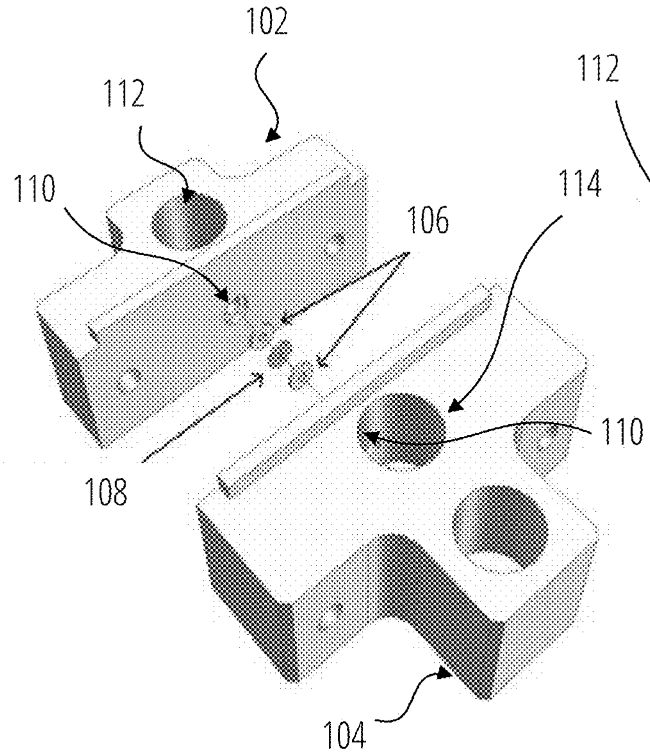
FIG. 1A illustrates a perspective overview typical cell from the prior art, with a nanopore containing membrane and reservoirs.

Unless otherwise noted, technical terms are used according to conventional usage.

As used in the specification and claims, the singular form "a", "an", or "the" includes plural references unless the context clearly dictates otherwise. For example, the term "a nanopore" includes a plurality of nanopores including mixtures thereof.

When a dimensional measurement is given for a part herein, the value is, unless explicitly stated or clear from the context, meant to describe an average for a necessary portion of the part, i.e., an average for the portion of the part that is needed for the stated purpose or function. Any accessory or excessive portion not necessary for the stated function is not meant to be included in the calculation of the value.

As used herein, "about" means within plus or minus 10%. For example, "about 1" means "0.9 to 1.1" and so on.

As used herein, the approximate symbol, i.e., "~", unless otherwise indicated, indicates that the discussed value is equal to the indicated value plus or minus 5% of the indicated value. As an illustration, if the test refers to "100±5%" the indicated value may range from 95 to 105.

As used herein, the term "biopolymer" refers to compounds that are important to biological and biochemical processes, and are multi-unit compounds made up of monomeric units. Generally, biopolymers are degradable and biocompatible. Examples of biopolymers are oligo- or polynucleotides (e.g., DNA, RNA), oligo- or polypeptides (e.g., protein, shorter peptides, collagen, actin, and fibrin), and oligo- or polysaccharides which are linear or branched chains of carbohydrates (e.g., starch, cellulose, collagen, alginate, sugars, charged or neutral carbohydrates, etc.). Lipids, which have extended carbon chains can, for the purposes of practicing the disclosed invention, be grouped with biopolymers. There are other polymers that are not biopolymers, e.g., petroleum-derived polymers which are widely used in industrial applications such as plastic-making.

As used herein, the term "cell" refers to an apparatus that holds and processes one or more fluidic samples employing a nanopore-containing membrane between at least two fluid reservoirs.

As used herein, the term "clog" (or "clogging") refers to where a nanopore's properties have been modified because a molecule type has been situated, either reversibly or permanently, on, near, or within a nanopore such that the ability of the nanopore to interact with some molecule type has been changed. Generally, clogging means that the nanopore's ability to transport some molecule type through pore has been diminished, but a change in the nanopore's ability to distinguish between two molecule types would also be considered clogging. In general, the indication of a clog is a change in what should be an open-pore current or current noise levels measured with respect to a nanopore.

As used herein "configuration," (or "configurational") with respect to a molecule, denotes either a particular geometry, diastereomer, or isomer of a molecule distinguishable from another geometry with regard to its influence on any property of a nanopore.

As used herein, "electrolyte salt" refers to a salt compound which disassociates in a liquid solvent to liberate cations and anions facilitating current flow upon the application of a voltage gradient.

As used herein, the term "freshly formed," or "nascent" refers to the state of a surface region that is void of significant oxide formation or other masking groups that would otherwise preclude substantive and intended chemical attachment to the underlying silicon or nitrogen atom(s). Accordingly, a "freshly formed" silicon surface or region has available silicon at sufficient density for chemical attachment. Similarly, a "freshly formed" silicon nitride surface or region has available amine ($Si—N—H_2$) at sufficient density for chemical attachment (e.g., by forming covalent Si—N—C bonds on the surface or region). Some oxide formation on a "freshly formed" silicon or silicon nitride surface/region is allowed within the meaning of the present invention as long as the intended chemical attachment or functionalization reaction can proceed and result in successful and significant surface modification. In a preferred embodiment, a "freshly formed" silicon or silicon nitride surface/region is provided without the use of any etching (e.g., hydrofluoric acid) treatment to strip oxides on the surface or region—such a surface may be provided directly through the nanopore fabrication technique called "dielectric breakdown."

As used herein, "functionalized," "functionalization" or the similar, refers to the modification of a molecule or material to alter its interaction with other molecule types or ions. Such modifications can include changes to charge distribution, steric properties, molecular orbital properties, etc. Other modifications might include changes which alter the molecule's response to light, applied voltage, surrounding pH, pressure, temperature, or binding to a second molecular type in the presence of a third molecular type.

As used herein, "functionalized pore" refers to a nanopore coated with at least a partial layer of bound molecules that alters how the pore surface interacts with other molecule types or ions. These bound molecules may be further functionalized by subsequent chemical modifications. Typically, such secondary functionalization is accomplished by modifying a terminal portion of the bound molecule.

As used herein, "molecule type" or "molecular type" refers to a chemical element or compound in molecular state or ionic state soluble in a chosen fluid which can be distinguished from another element or compound using an intrinsic physical property. For example, charged molecular types could be distinguished from uncharged molecular types by employing a mechanism based on charge, or a large molecule type might be distinguished from small molecule type by a mechanical process. A molecule type might refer to a stereo-isomer of the same chemical compound because the different isomers could be distinguished from one another by one type's affinity differing from another type's affinity to a third chiral chemical. A molecule type also might be distinguished from another type by molecular configuration.

As used herein, "nanopore" refers to a hole or opening in a membrane or film of a diameter between about 0.5 nm and about 100 nm which fully penetrates the membrane or film. At this scale, the behavior of liquids can change, and the relative effect of structural or electronic changes to the atoms or molecules interior to the nanopore may increase dramatically. These interfacial properties of the nanopore are long-scale relative to the pore's cross-section, and provide the potential to fully and dynamically control mass transport with single molecule precision.

As used herein, the terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded.

The term "photo-isomer" herein refers to molecular configurations achieved by radiating a photo-responsive molecule with light radiation, e.g., with wavelength in the visible (to human) or ultraviolet range. In preferred cases, exposure to light of a chosen wavelength can cause a molecule to predictably and stably assume a particular configuration. In some cases, subsequent exposure of the same molecule to the same or different radiation can convert the molecule to a different configuration. Note that as used herein, photo-isomers can, in some cases, act similar to chemical isomers, where molecules of the same empirical formula vary by bond topology. In other cases, photo-isomers retain their bond topology, and only the geometrical configuration of the molecule changes as a result of changes in the orientation of a part or parts of the molecules. Photo-isomers can be quite stable, e.g., by holding a configuration for half-lives as long as days at room temperature. Also significant is that properties that photo-isomers have in bulk generally can be retained when photo-isomers are constrained to nanopore scale. These facts allow photo-isomers to form the basis of reversibly configurable nanopores when photo-isomerizable molecules are bound to a nanopore's interior. See "configuration" above.

As used herein, "photo-isomerizable" refers to a molecule being capable of assuming different photo-isomers.

"Photoswitch" herein refers to the act of converting a photo-isomerizable molecule between various configurations of its photo-isomers.

As used herein, "pore properties" refers to physical properties of a nanopore which are significant at nanoscale. These properties are diverse, including (but not limited to) pore diameter, pore thickness, surface coating, base material (substrate), charge characteristics, steric properties of molecules bound to the interior of the pore, the response of a surface material to pH, charge, solvent, temperature, electrolytes, analytes, the voltage applied to or the current carried through the pore. A specific set of pore properties will allow different molecular types to pass through the pore while rejecting other molecular types.

As used herein, "pore-voltage-gradient" refers to the profile, as a function typically defined along the axis defined along the pore entrance to the pore exit, of a voltage potential. The potential is frequently applied externally with the goal of powering active transport of solvent or molecular types through a pore.

As used herein, "resistive-pulse sensing" refers to a change in measured voltage or current across a pore in which each pulse corresponds to the passage of one or more molecules though a pore. For resistive-pulse sensing to work well, the baseline noise level must be low enough to have sufficient signal to noise ratio, plus the pore properties must be reasonably stable over the measurement period.

As used herein, the term "silicon nitride" refers to any chemical compound consisting substantially of two elements only: silicon and nitrogen, such that it can be chemically represented as $Si_xN_y$ or $SiN_x$ for simplicity. The most thermodynamically stable amongst silicon nitride ($Si_xN_y$) is $Si_3N_4$. A "silicon-rich" silicon nitride, as used herein, refers to a silicon nitride ($Si_xN_y$) where the ratio of "x" over "y" is greater than 0.75, i.e., x:y>3:4, e.g., where "y" is 4, "x" can be 4, 5, 6, 8, or more. Other examples of "silicon-rich" Si/N ratio in silicon nitride include: 0.77, 0.82, 1.02, 0.95, 1.14, 0.87, and so on (see Journal of Vacuum Science & Technology A: Vacuum, Surfaces, and Films 14, 2879 (1996)). A silicon nitride substrate can be one or more layers of silicon nitride deposited on a semiconductor (e.g., silicon) base.

As used herein, "small molecule" refers to an organic compound having a molecular weight less than, or approximately, 1000 Daltons.

As used herein, "stable" refers to a pore which is controllable by altering its pore properties, which exhibits a current flow under an applied pore-voltage-gradient such that a good signal-to-noise ratio can be achieved for resistive-pulse sensing and which does not clog during a suitable operational period, e.g., more than 30 minutes, an hour, a day, etc.

As used herein, "translocation" refers to the transport of a molecular type from one side of a nanopore through and out of the nanopore to the other side. The motive force could be diffusion, osmosis, electroosmosis, electrophoresis, or a combination of these. Other than pumping applications where the goal is simply changing concentrations or mass transport, a set of translocations can function to characterize (distinguish between), sort, separate, or isolate, molecular types from one another. In the case of characterizing or discriminating, the event of translocation can function as a 'read' operation to extract information from molecular type. Read operations on genetically encoded molecules could enable extremely rapid genome sequencing, and in proteomics (for instance, through transcription). Read operations on molecular types from certain families of chemicals, such as carbohydrates, could enable extraordinarily dense data storage and retrieval technologies.

EMBODIMENTS

Photo-regulated nanopore sensors of the instant application are comprised of a nanopore-containing membrane substrate having interior and exterior surfaces with a photoswitch covalently affixed to the interior surface thereof that defines the nanopore. In some embodiments of the invention, the nanopores of the invention exhibit certain select properties including, but not limited to, high melting point, chemical inertness and/or controlled chemical reactivity, high thermal stability, high shock resistance and optical nonlinearities. The nanopores may be manufactured using a number of materials including, but not limited to, petroleum-derived polymers including, but not limited to, polycarbonate, polyethylenimine and polyimide and/or thin-film materials including, but not limited to graphene, silicon, silicon oxide, silicon nitride, and hexagonal boron nitride. In a preferred embodiment, silicon nitride is used. The nanopores may also be manufactured using transition metal dichalcogenides, such as molybdenum disulfide, molybdenum diselenide, tungsten disulfide and tungsten diselenide. MXenes, including mono and double transition MXenes and divacancy MXenes, are also potential manufacturing materials.

In a preferred embodiment, the photoswitch, a photo-isomerizable compound, forms a monolayer and is affixed to the interior surface of the membrane defining the nanopore. The monolayer may cover the entire length of the interior surface or a substantial portion thereof. The photoswitch is designed to adjust the photo-regulated nanopore to sense desired molecules. In the preferred embodiments, those molecules are biopolymers such as DNA and complex carbohydrate biopolymers including, but not limited to, neutral carbohydrates, charged complex carbohydrates, proteins and lipids; and the photoswitch may be configured so that the same photo-regulated nanopore senses different, target molecules at different times. The photoswitch may be selected from the group consisting of spiropyrans, hydrazones, donor-acceptor Stenhouse adducts, stilbenes, azobenzene derivatives, diarylethenes and derivatives thereof, and dithienylethenes and derivatives thereof.

Such a monolayer may be created within a nanopore formed on a silicon-rich silicon nitride surface or a silicon surface in nanopore fabricated through dielectric breakdown techniques such as those described by Dwyer, J. et al. (2019), Covalent Chemical Surface Modification of Surfaces with Available Silicon or Nitrogen, (U.S. Pat. No. 10,519,035) and incorporated herein by reference.

The photo-regulated nanopore sensors generally have a diameter between about 1 and 100 nm, e.g., between about 1 and 10 nm or 10 and 25 nm or 25 to 100 nm, and preferably between about 1 and about 20 nm. Various processes may be employed to manufacture the novel photo-regulated nanopore. These processes include, but are not limited to, heavy ion bombardment, electron-milling, helium milling and focused ion beam (FIB) milling. The process to manufacture a preferred embodiment is discussed in more detail below.

Figure 1B:
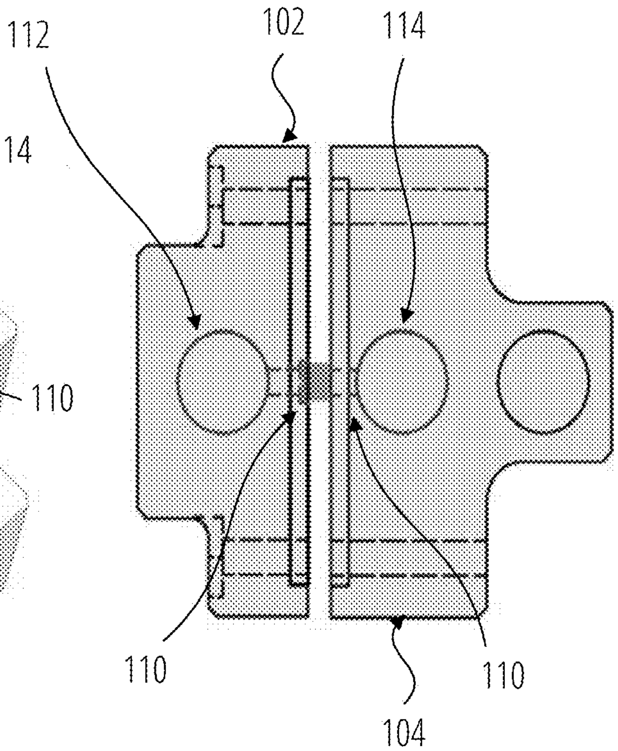
FIG. 1B illustrates a top-down cross-section of a typical cell from the prior art showing the connections between a nanopore containing membrane and reservoirs.

FIGS. 1A and 1B illustrate a cell with a nanopore-containing membrane and reservoirs that serve to illustrate structural configurations of a translocation device, more specifically, a molecular sensor according to an embodiment of the invention. The cell's overall structure is shown in FIG. 1A and gives an overview of how the cell is made from a Left Cell Frame 102 bolted to a Right Cell Frame 104 sandwiching a Nanopore Chip 108 between the frames and Nanopore Chip Gaskets 106. Source 112 and target 114 reservoirs are in fluid communication with the Nanopore Chip 108, allowing mass transport by fluid movement, by means of channels 110. Conventional additions, such as valves (e.g., one-way valves), removable chambers, fluid and electrical attachments are known in the art and employed for convenience in any given application.

In a preferred embodiment, nanopores were formed by controlled (dielectric) breakdown in 15 nm-thick $SiN_x$ membranes and then functionalized by photohydrosilylation with an azobenzene derivative having the structure:

(Formula 2)

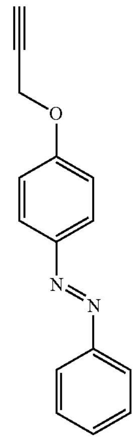

4-(propargyloxy)azobenzene

Figure 5:
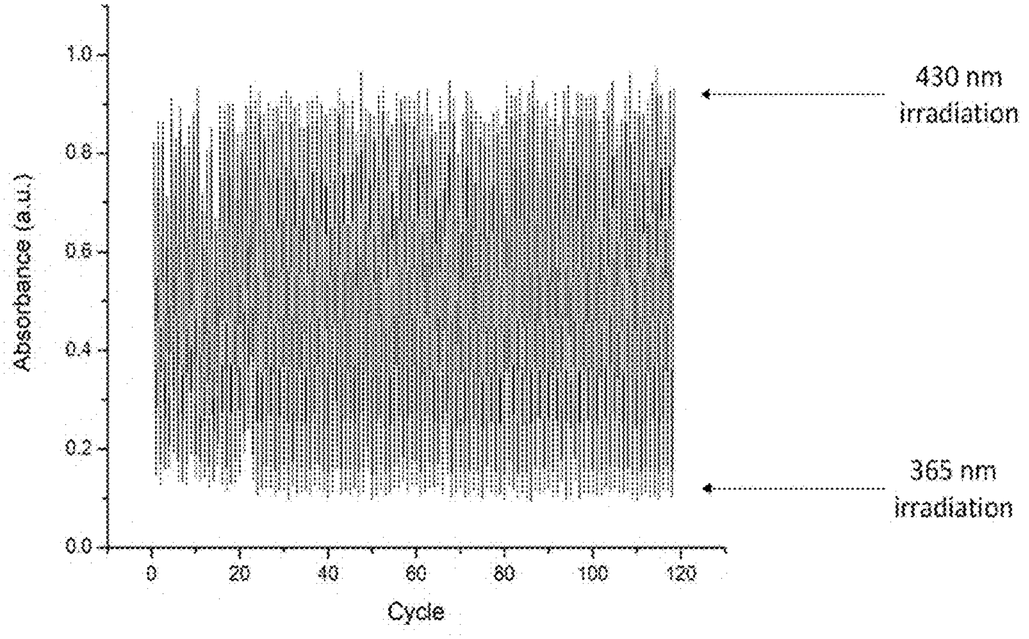
FIG. 5 is a graph of the reversible photo-switching of the 4-(propargyloxy)azobenzene for more than 100 cycles in free solution. In particular, the irradiation graph (absorbance (a.u.) v. cycle) reports the absorbance change of 4-(propargyloxy)azobenzene monitored at 338 nm during cycling between cis-rich (365 nm) and trans-rich (430 nm) states in acetonitrile. Each cycle was recorded for 15 seconds of irradiation. Thus, the nanopore structure is robust enough for repetitive operation.
Figure 6A:
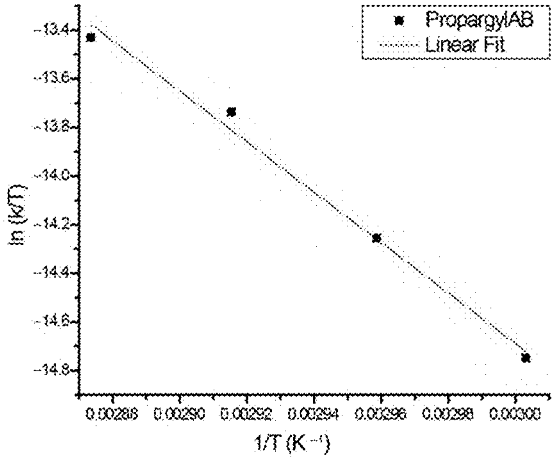
FIG. 6A and FIG. 6B are Eyring plot analysis graphs of the cis-to-trans thermal reversion of 4-(propargyloxy) azobenzene monitored in FIG. 6A acetonitrile at 60, 65, 70 and 75° C.: ΔH ‡=86 kJ/mol; ΔS ‡=−61 J/(mol·K) so that at 298.15 K, ΔG=104.5 kJ/mol, $t_{1/2}$/ln2/k=61 h, and FIG. 6B 1M KCl/10 mM HEPES solution at 60, 65, 70, and 75° C.: ΔH ‡=83 kJ/mol; ΔS ‡=Δ68 J/(mol·K) so that at 298.15 K, ΔG=103.4 kJ/mol, $t_{1/2}$/ln2/k=41 h.
Figure 6B:
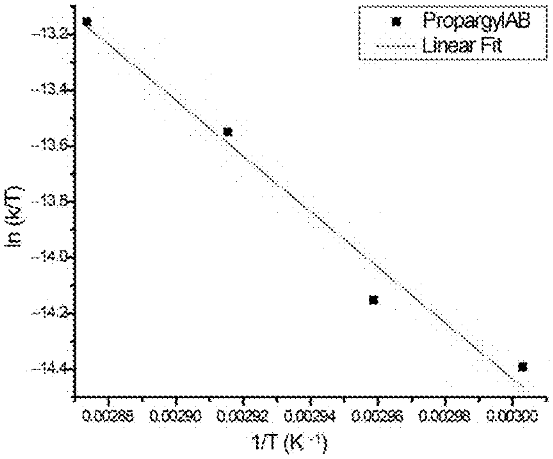

Nanopore conductance in molar-ionic-strength solutions is essentially determined by the nanopore dimensions as follows:

$$G=\sigma(4l/\pi d^2+1/d)^{-1} \quad \text{Eqn (1)}$$

where d and l are the nanopore diameter and length, respectively, and σ is the solution conductivity (Kowalczyk S W et al., (2011), Nanotechnol, 22(31):315101). After coating, the effective physical diameter of the nanopore is reduced by about twice the thickness of the molecular film, $t_{film}$: $d_{with\ film}=d_{SiNx\ only}-2\cdot t_{film}$. The ~7.4 nS conductance decrease after photohydrosilylation of a 10.5 nm-diameter nanopore corresponded to a diameter change of 1 nm. This is consistent, within typical measurement accuracy with the successful installation of no more than a monolayer of the 4-(propargyloxy)azobenzene on the surface of the pore (FIG. 2A). Reversible photo-switching of the 4-(propargyloxy)azobenzene for more than 100 cycles in free solution was demonstrated (FIG. 5). Thermal stability studies of the cis 4-(propargyloxy)azobenzene in free solution demonstrated its room temperature half-life to be 61 hours and 41 hours in the organic solution used for photo-switching and aqueous electrolyte used for measurements, respectively (FIGS. 6A and 6B). No solvent-induced impediments to thermally stable isomerization of the nanopore coating was observed. Unlike a photochromic coating on the outer surface of a nanoparticle where the free end of the molecule is further away from its neighbors, for example, the attachment of a molecule inside a nanopore means that the free ends of the molecule will all tend to be more sterically crowded than at the surface.

Figure 7:
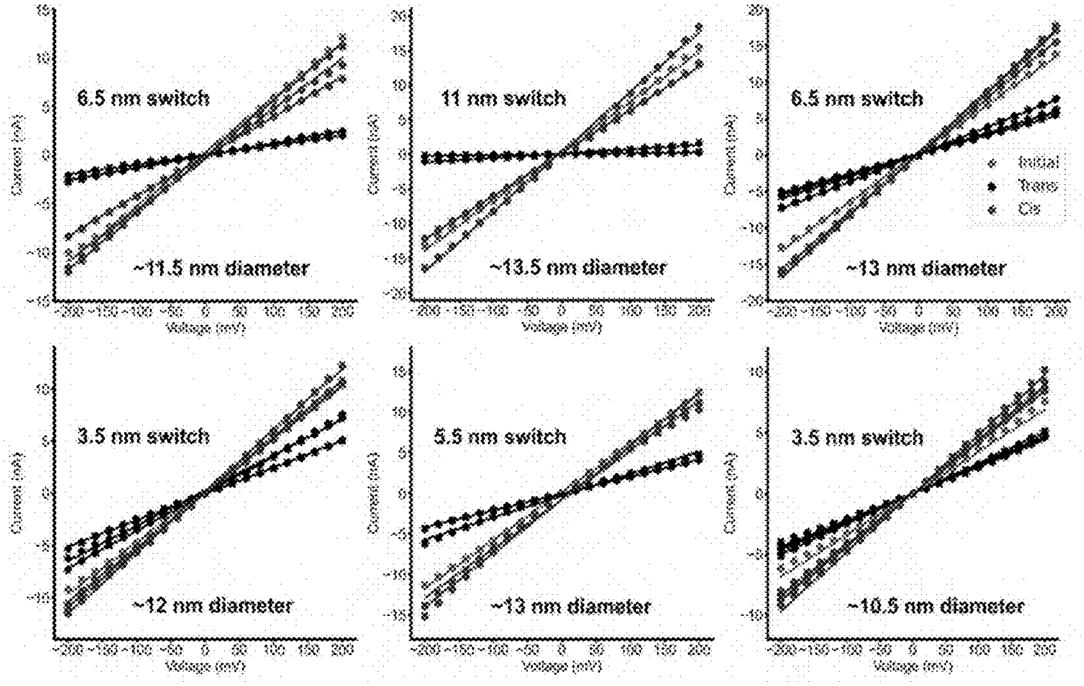
FIG. 7 is a collection of graphs for six independent functionalized pores reporting on the change of conductance of each pore observed after irradiation thereof with visible light that caused a significant increase in conductance. The cycle was repeated between these two distinct low and high conductance states Each unique, independent functionalized pore shown went through several switching events. Before and after each event, an IV curve was collected to characterize resulting change in the pore's conductance, showing these nanopores can be reliably constructed with controllable properties.

In this embodiment, it was observed that 4-(propargyloxy)azobenzene, once affixed to the nanopore interior surface as a monolayer in accordance with the instant invention, remains photo-responsive by optically selecting both the monolayer thickness (FIG. 2A) and the nanopore conductance (in accordance with Eqn. 1). For example, irradiation of a trans monolayer with 365 nm (wavelength) photons in the UV range reduces the nanopore's effective diameter and conductance via trans→cis isomerization, and cis→trans isomerization driven by visible light irradiation increasing the diameter and conductance (FIG. 2B). Experimentally, irradiation with 365 nm UV light after the nanopore surface coating step caused a significant decrease in conductance (FIG. 2C). Irradiation with visible light then caused a significant increase in conductance. The cycle was repeated between these two distinct low and high conductance states (FIG. 2A, and FIG. 7). This behavior was fully consistent with a functional photochromic nanopore cycling between cis and trans isomers. Visible light drove a cis-to-trans isomerization that reduced the nanopore diameter thereby also reducing the conductance while UV light drove a trans-to-cis isomerization that increased the nanopore diameter and its conductance. With changes in conductance, the pore-voltage gradient also changes, providing a reliable way to distinguish or sense a molecule type through resistive pulse sensing.

Figure 4A:
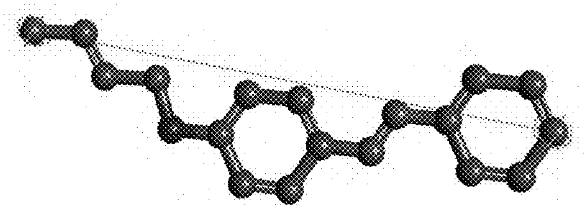
FIG. 4A is the structure of the trans-azobenzene with a 1.47 nm distance from anchor to surface-distal terminus point.
Figure 4B:
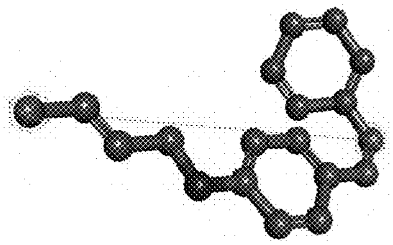
FIG. 4B is the structure of the cis-azobenzene with a 1.05 nm distance from anchor to surface-distal terminus point. These two distances are used as the thickness of a monolayer of each configuration, providing a characteristic scale for which the nanopore can effectively function.
Figure 8A:
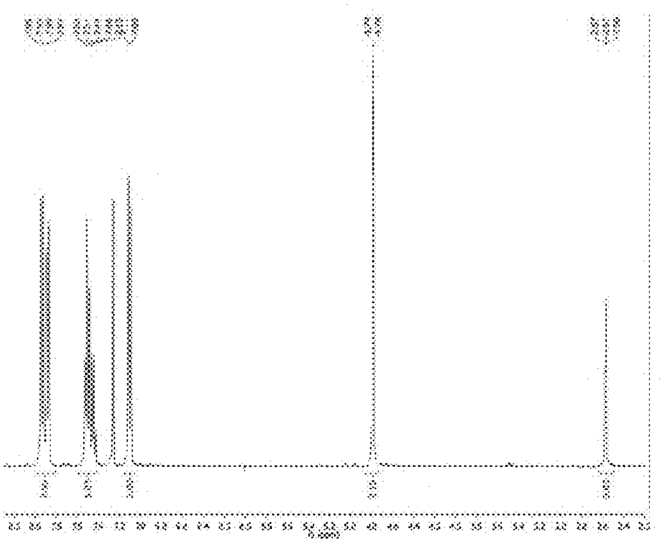
FIG. 8A and FIG. 8B are NMR spectra for the as-synthesized 4-(propargyloxy)azobenzene (FIG. 8A) and under photohydrosilylation irradiation conditions in bulk acetonitrile solution (FIG. 8B).
Figure 8B:
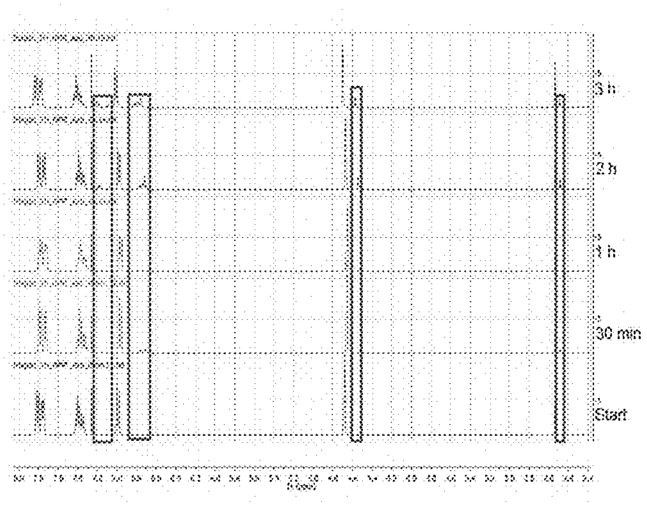
Figure 8C:
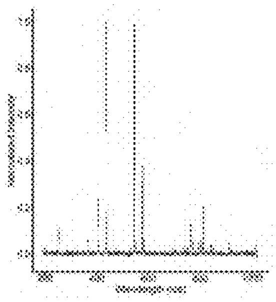
FIG. 8C shows the UV/Vis spectrum of the mercury lamp used.
Figure 9:
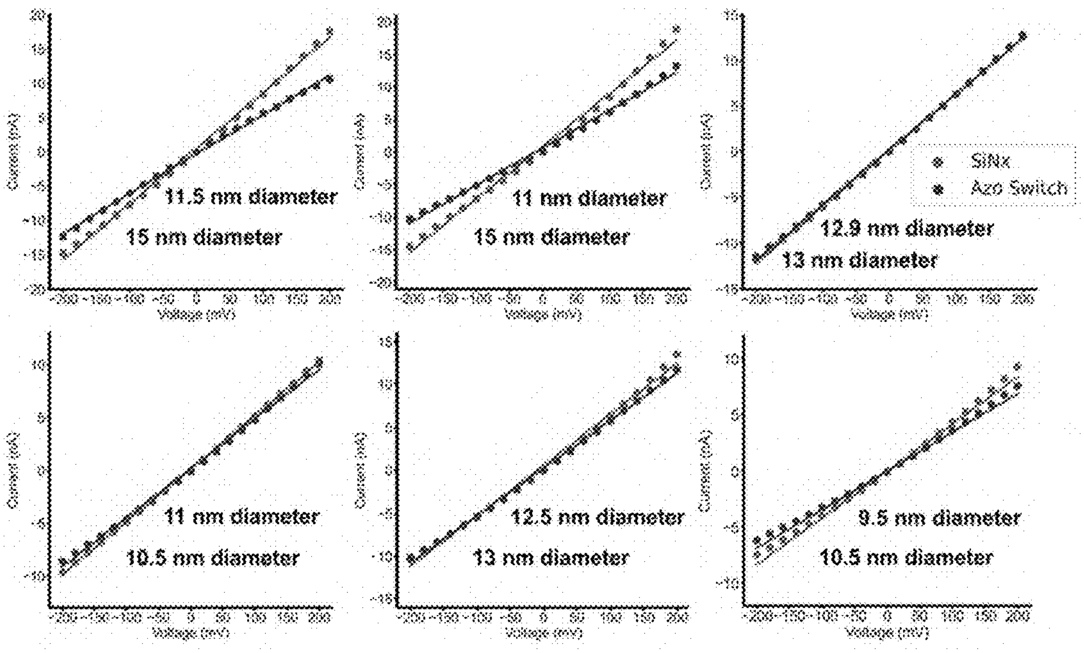
FIG. 9 shows IV curves collected for each nanopore before and after functionalization. The nanopore characterized in each plot is the same nanopore by row and column showing photochromism, showing a correlation between pore size and pore function.

Photoattachment of the nanopore coating was initiated using the trans conformer, but the conductance of the initially photohydrosilylated nanopore was substantially in agreement with the more open of the two states. Solution-based experiments show that the spectrum of the unfiltered mercury lamp used for photohydrosilylation additionally drives trans→cis isomerization (FIG. 8A). Given the prominence of nanopore diameter (and thus film thickness) in determining nanopore conductance, the film is thus likely present in the predominantly cis configuration in spite of the low apparent trans→cis conversion in bulk studies (FIG. 8A). Preferential transport of the cis conformer to the nanopore interior and longer residence time within the pore by partitioning or covalent coupling both would allow for this local enrichment of the cis isomer. Once the film was deliberately switched to the trans configuration using one of the photoswitching light sources, all subsequent conductance changes conformed to the molecular mechanism-derived expectation (FIG. 2A, FIG. 8A). In several instances, the initial conductance of the nanopore after photohydrosilylation was essentially indistinguishable from that of the unfunctionalized nanopore (FIG. 9). This result provides no definitive evidence of a coating and would be more suggestive of a failure of the surface coupling reaction. And yet the conductance could be photoswitched to a larger value and subsequently cycled with optical control between two states (FIG. 7, FIG. 9) as already described and detailed in FIG. 4A and FIG. 4B.

Figure 10:
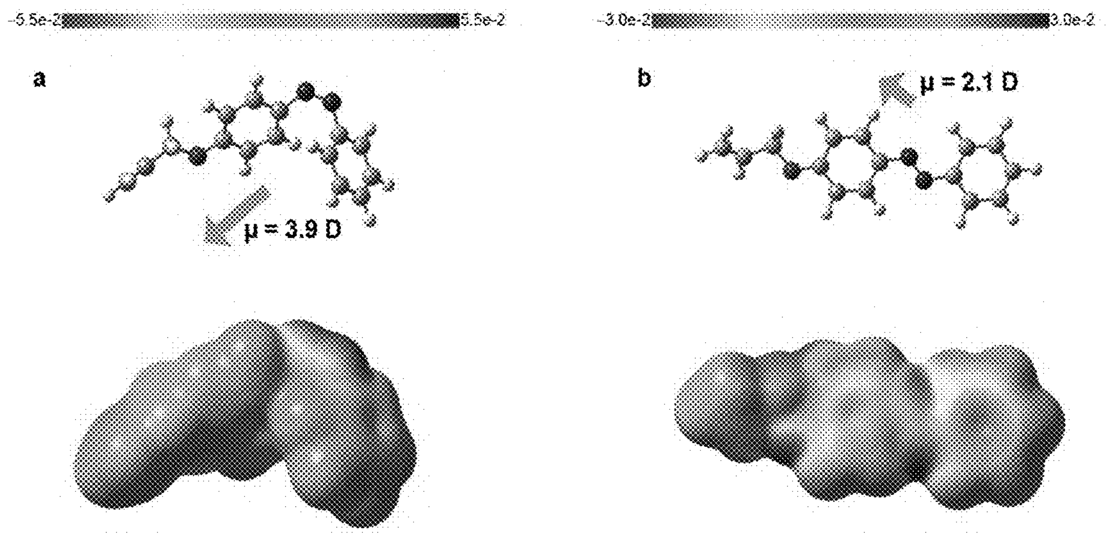
FIG. 10 depicts atomic models and electrostatic maps of the 4-(propargyloxy)azobenzene in (a, c) trans and (b, d) cis configurations, providing a sense of how the steric footprint of the molecule varies between the two photo-isomeric states.
Figure 11A:
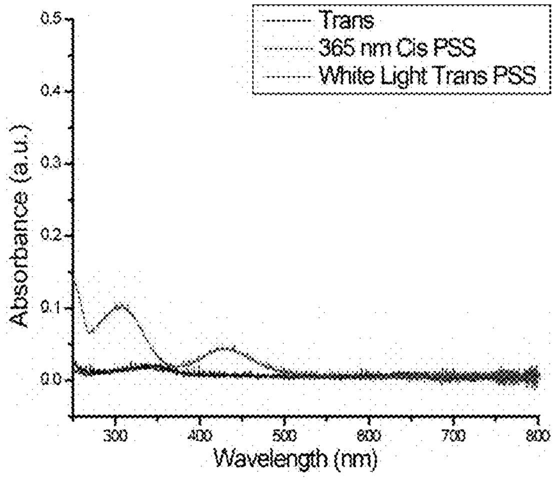
FIG. 11A, FIG. 11B, and FIG. 11C are UV-Vis absorption spectra for 4-(propargyloxy)azobenzene in FIG. 11A 1 M KCl/10 mM HEPES solution and FIG. 11B acetonitrile at the photostationary state under the irradiation at the indicated wavelengths at FIG. 11C is a UV-Vis absorption spectra of 4-(propargyloxy) azobenzene in 1 M KCl/10 mM HEPES solution at the photostationary state under irradiation at 365 nm, upon thermal reversion to 75° C., and upon cooling to 25° C.
Figure 11B:
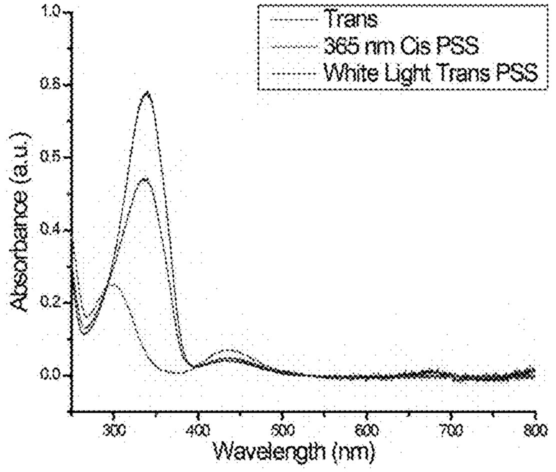
Figure 11C:
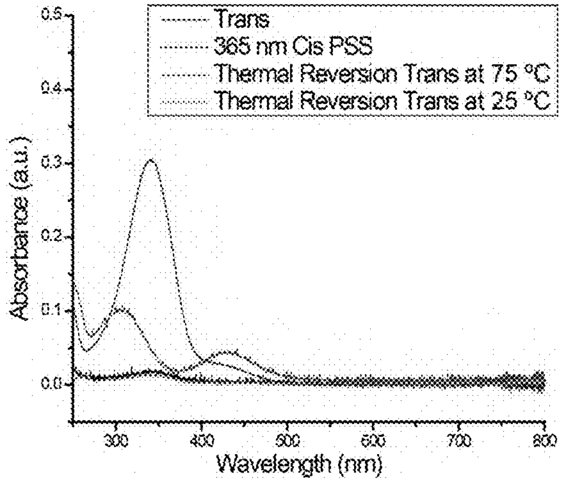

The azobenzene derivative employed in the present invention offers two distinct nanopore coatings without changes in chemical formula or structure other than isomerization about a double bond. The isomerization provides a means to control the film thickness and nanopore conductance. There is, unlike for some photochromic species, no change in the discrete formal charges on the molecule during isomerization in the pH range of interest ($pK_a$ trans-azobenzene −2 to −3, cis-azobenzene −1.5). Each configuration of the azobenzene, however, presents a different charge distribution at the interface between the nanopore surface and solution—and to any proximal analyte molecule (FIG. 10). The trans isomer is largely hydrophobic with a dipole moment of 2.0 D whereas the cis isomer is more hydrophilic with a dipole moment of 3.9 D, according to DFT calculations of each isomeric structure. This large polarity change of the azobenzene coating will affect the nanopore wetting. The 4-(propargyloxy)azobenzene moiety in the ground state (trans) is mostly insoluble in aqueous solutions (or organic solvents) and forms aggregates in bulk solution, as illustrated in the UV-Vis absorption spectrum (FIG. 11A). The aggregates undergo photo-induced isomerization and then, as a result of the increased hydrophilicity of the cis isomers, undergo subsequent dissolution in the aqueous solution. The absorption spectrum of the cis photo-isomer in aqueous solution displays the characteristic absorption bands of a cis state ($\pi$–$\pi$* at 310 nm and n–$\pi$* at 430 nm) consistent with those recorded in organic solutions (FIG. 11B). The solubilized cis isomers switch back to trans upon white light irradiation or thermal activation then precipitate (FIG. 11B, FIG. 11C). These observations, in bulk solution, illustrate the solvation state of the azobenzene molecules in each isomeric form that are used to coat the interior of the nanopore and suggest that these effects would have similar effects within the pores. The strong $\pi$-$\pi$ interactions among the neighboring trans isomers lead to the aggregation of pendant azobenzenes and create a hydrophobic surface, whereas the solvated, polar cis isomers lower the surface tension between the azobenzene layer and the ionic solution. This can affect the apparent nanopore size. Models like Eqn (1), currently known in the art, do not account for wetting. This could explain the cis enrichment and even the lack of change in nanopore diameter, e.g., if the cis lay down flat against the anionic nanopore surface. Given this behavior of the free 4-(propargyloxy)azobenzene in bulk aqueous solution and the complexities that can be presented by nanopore confinement, it was predicted that photoswitching the nanopore in ultrapure water could be achieved. Indeed, FIG. 12A demonstrates that the switching is feasible for the surface-attached, nanoconfined photoswitch in aqueous solution.

Figure 13A:
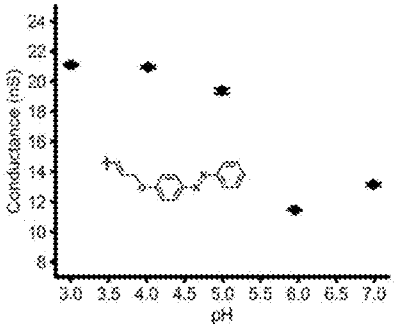
FIG. 13A and FIG. 13B shows conductance (G) vs pH curves for nanopores in the trans FIG. 13A and cis FIG. 13B configurations. An increase in conductance was observed under more acidic conditions in both cases, hypothesized to be from an increase in surface charge density due to protonation of the azo group.
Figure 13B:
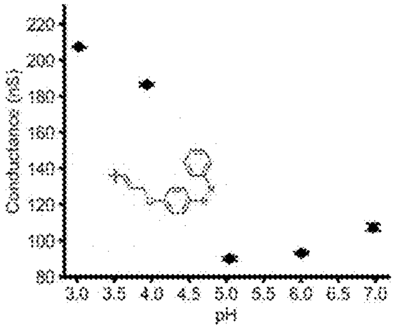

An unfunctionalized $SiN_x$ nanopore surface is comprised of a mixture of surface —OH and —$NH_2$ groups. It would be neutral at pH ~4.3 (—$O^-$ and —$NH_3^+$), positively charged at more acidic pH (—OH and —$NH_3^+$) and negatively charged at higher pH values (—$O^-$ and —$NH_2$). This change in surface charge with pH changes the conductance at the same time. For $SiN_x$, there would be a minimum in the conductance at the isoelectric point (pI ~4.3) with the higher conductance values at more and less acidic pH values because the surface is charged. The conductance of the same photochromic nanopore in both configurations as a function of pH was measured (FIGS. 13A and 13B). A transition between two regions of opposite slope and measurements using maltodextrin at pH 7 (vide infra) indicated a positively charged surface in the less acidic region of the chart. The measured curves showed no dramatic departure from the general behavior of the bare $SiN_x$ pore surface. Since the 4-(propargyloxy)azobenzene is not amphoteric and the cis conformer and isomerization reaction must be sterically accommodated, it is reasonable to consider that the photochromic film leaves underlying $SiN_x$ exposed to the solution. The change of conductance versus pH would then be less completely dominated by the surface coating properties as in previous work with alkyl chains. The measured curve minima, however, are different for cis and trans films. The curve for the trans film showed less concordance with the curve for bare $SiN_x$ than the cis film. The trans film created a more hydrophobic local surface environment for any unprotected $SiN_x$ and the smaller pore diameter amplified its influence on the nanoconfined solution structure that is the means by which the surface charge is detected through conductance.

Figure 12A:
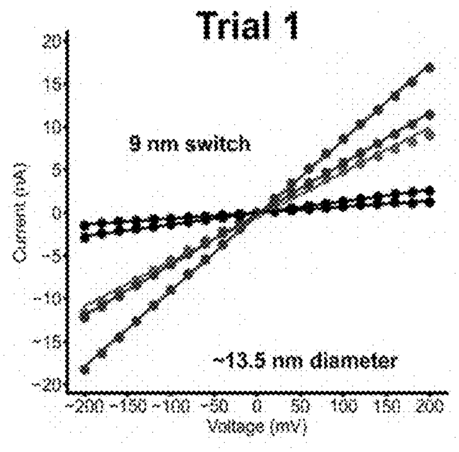
FIG. 12A and FIG. 12B graphically depict the switching of the 13.5 nm FIG. 12A and the 9 nm FIG. 12B diameter nanopores in ultrapure water demonstrating the potential for in situ switching without removing or changing solvent from the fluidic cell.
Figure 12B:
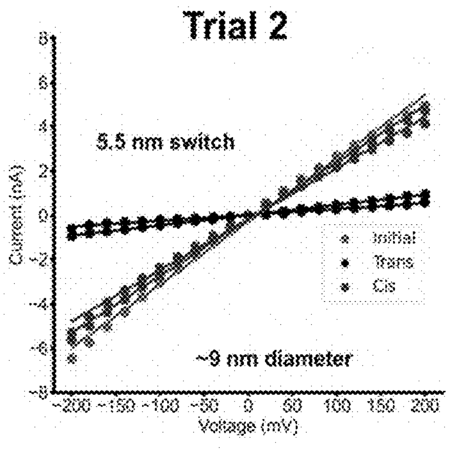

In all cases, once a functional photochromic nanopore surface coating was formed, the conductance is definitively and controllably photo-switched between two readily distinguishable states. Switching between the 1.47 nm trans film thickness and the 1.05 nm cis film thickness (FIG. 2A, FIG. 4A, FIG. 4B) would change the nanopore diameter by ~0.84 nm. The change in diameter for the ~80 nS high-conductance state of FIG. 2A to its ~30 nS low-conductance state is ~6.5 nm. This is consistent, within typical measurement accuracy, with the predicted ~0.84 nm-diameter change. The change in film thickness remains consistent with results for switching in pure water (FIG. 12A). These two distinct conductance states, supporting ~15.5 and ~5 nA current flows through the pore were stable across a 30-minute measurement time in the presence of high electric fields (up to ~200 mV/15 nm≅13 mV/nm) across the nanopore. This evidenced that a photochromic thin film nanopore that maintained the bistable states, trans and cis, during the measurement period was created. Such a nanopore can be used, as is known in the art, as a digital memory bit for reversible nondestructive data storage with readout of the state by ionic conductance and setting of the state by photons of the appropriate wavelength.

Rather than direct use as a memory bit, nanopores with photoselectable size (effective diameter), polarity (charge distribution, or dipole moment), and conductance have an even broader potential range of application as components in nanosystems. Others have pointed out how nanopores can be used as the readout element in DNA data storage schemes (Chen K et al, (2020), Nano Lett, 20(5):3754-60; Rutten M et al., (2018), Nat Rev Chem, 2:365-81). Accordingly, a switchable nanopore of the instant invention offers technological advantages including, for example, the potential ability to turn readout off until switched on, or to characterize the same biopolymer through two different states of the same pore. In other aspects, nanopores are important as enabling tools for biomedicine, particularly by exploring the performance of the photochromic nanopore for single-molecule sensing of biopolymers such as anionic DNA and complex carbohydrates. The complex carbohydrates can take on a greater range of chemical composition, charge, and structure than DNA (and thus can encode information more densely). But more broadly and significantly, the capabilities of photochromic nanopores in sensing the domain of genomics and glycomics are substantial.

Figure 3:
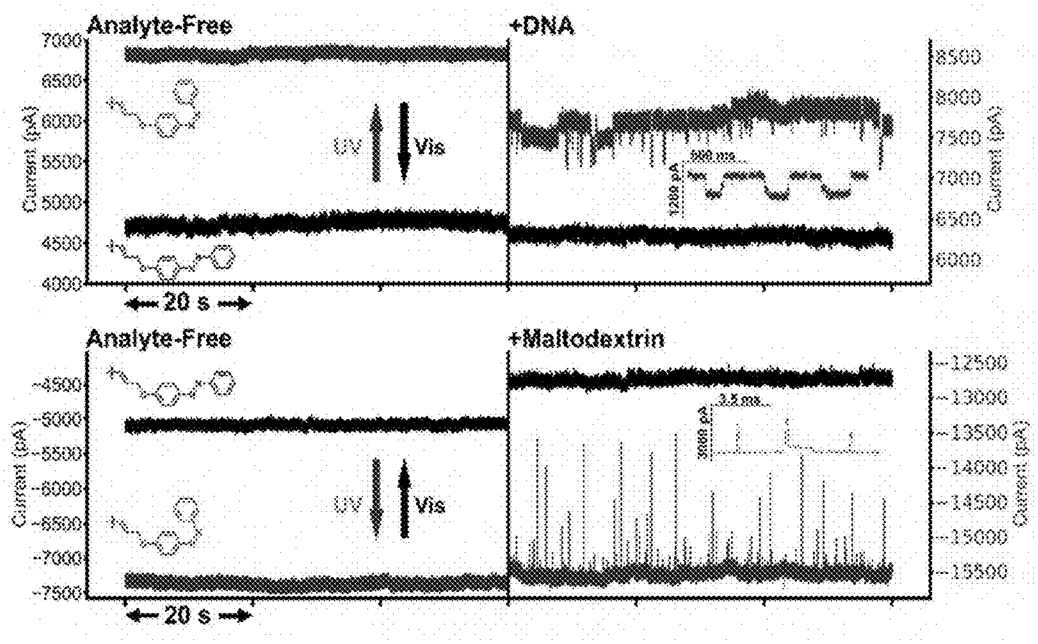
FIG. 3 illustrates that the cis and trans configurations of the monolayer and reversing the voltage polarity turned the nanopore sensing on and off for two different molecules: maltodextrin, a neutral complex carbohydrate polymer, and 3 kbp dsDNA, an anionic biopolymer. All current traces were acquired using a 200 mV applied voltage but with positive polarity for DNA and negative polarity for maltodextrin. Absence of analyte gave a steady baseline current. Addition of analyte to the pores with monolayer in the cis configuration resulted in readily detectable current spikes where each spike corresponded to the detection of a single molecule of that analyte. No such single molecule detection events were apparent with the monolayer in the trans configuration. A number of representative single-molecule current perturbations in each current trace, show that the nanopore functions to filter molecules with specificity.
Figure 14:
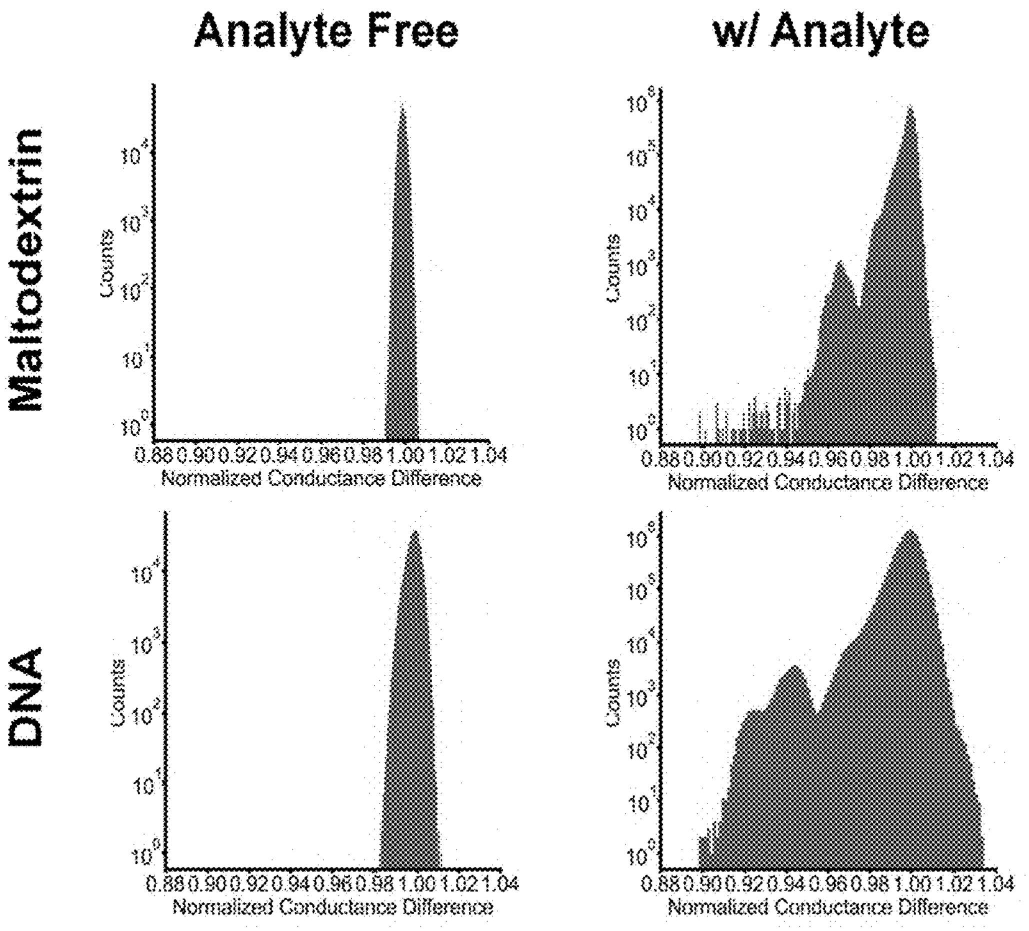
FIG. 14 is a collection of normalized conductance histograms for experiments with and without an analyte. Using a custom algorithm written in Python (Python 3.8, Python Software Foundation, Wilmington, DE), conductance traces were broken up into 200 ms windows, the conductance values in these windows were histogrammed, conductance values from events were filtered out, the filtered baseline conductance was re-histogrammed, and the max conductance was set as the average baseline. The average value of all average baseline values was used to normalize the counts peak of the highest conductance to 1.
Figure 15:
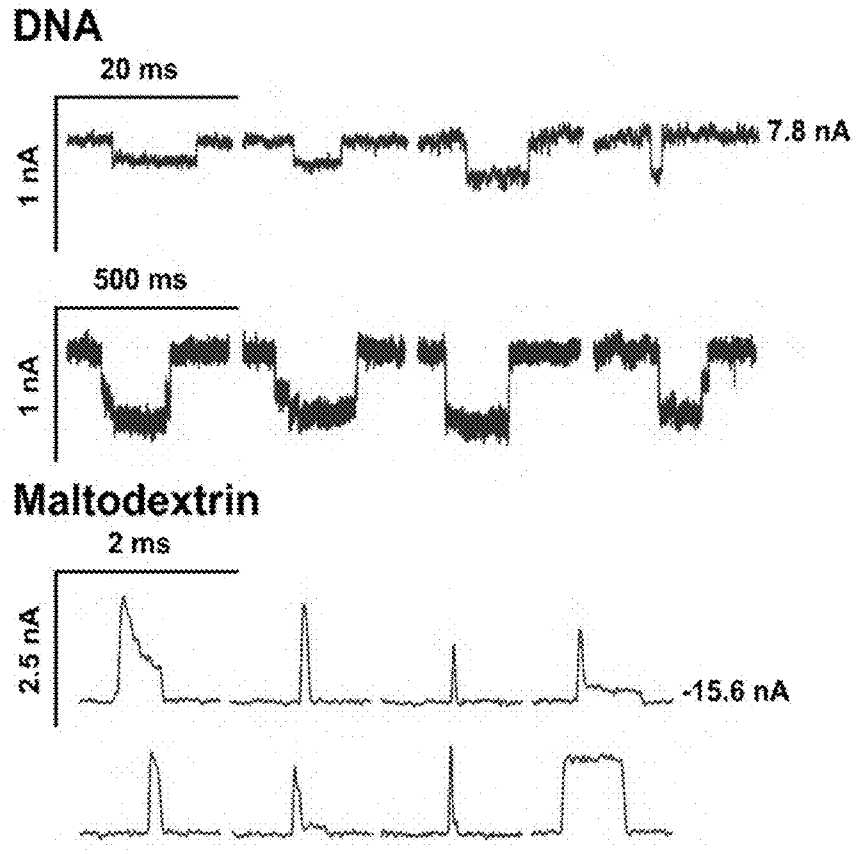
FIG. 15 graphically represents characteristic events for each analyte in 1 M KCl buffered at pH 7 with 10 mM HEPES. Since DNA is negatively charged, it translocated by electrophoretic forces. Detection occurs at opposite voltage polarities for each analyte as discussed in the main text.
Figure 16:
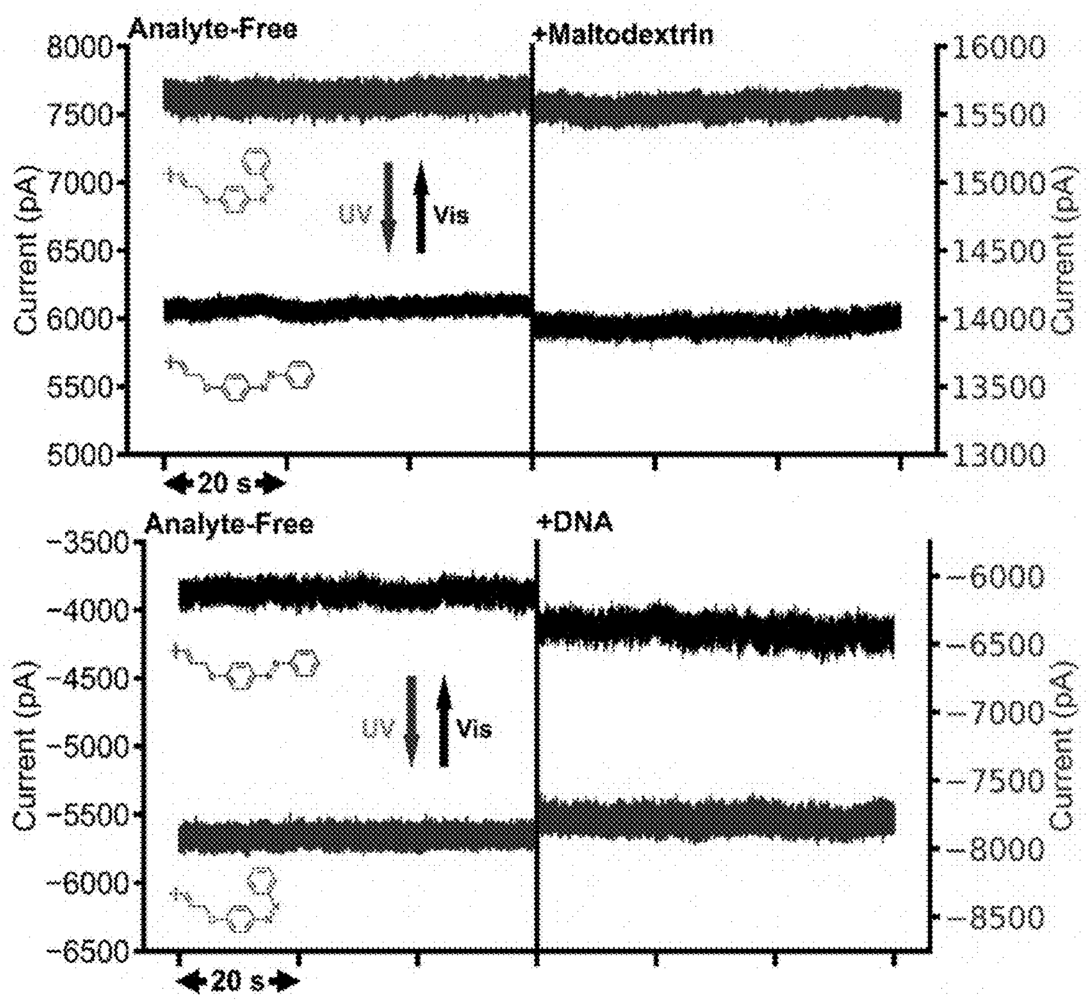
FIG. 16 graphically illustrates the suppression of detecting each analyte (maltodextrin and DNA) by the photo-regulated nanopore using the opposite voltage polarities with respect to the correct applied voltage polarity for successful detection.
Figure 17:
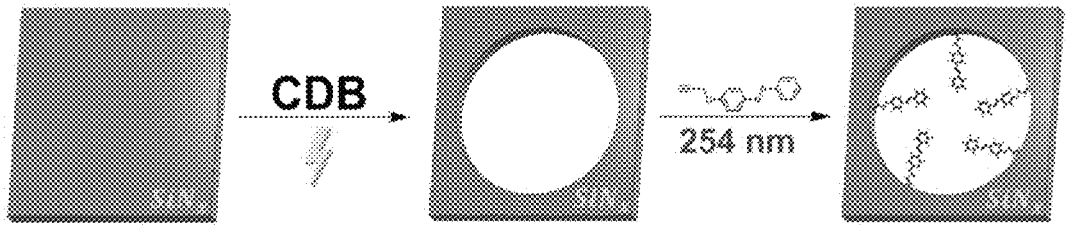
FIG. 17 depicts a schematic diagram of the process in which to fabricate the novel photo-regulated nanopores using voltage-induced controlled dielectric breakdown (CDB) in buffered electrolyte and covalently functionalizing the azobenzene photoswitch by photohydrosilylation in acetonitrile solvent.

For conventional biopolymer analysis by resistive-pulse sensing, the nanopore must be of a fixed size, it must provide a stable open-pore current, and it must allow an analyte of interest to perturb that open-pore current. Traditional nanopores fail in this implementation because they etch or clog, or because surface chemical fluctuations introduce too much noise during operation. Most organic molecular surface coatings are already a more structurally dynamic surface than an uncoated solid-state nanopore surface such as $SiN_x$ or graphene. Fortuitously, the azobenzene-coated nanopores in both cis- and trans-configurations presented steady open-pore ionic currents in the absence of analyte (FIG. 3). With the azobenzene in the trans configuration, addition of analyte—be it DNA or maltodextrin—to the nanopore flow cell did not alter the steady nature of the open pore current: there were no discrete transient current blockages. In other words, in a resistive-pulse sense, the trans pore was nonresponsive to both analytes. In contrast, the cis nanopore was responsive to both analytes with single-molecule-characteristic discrete blockages in the current trace of FIG. 3. Cumulative data from ~10 minute scans is shown in FIG. 14, along with a number of examples of discrete current blockage transients that were isolated from the open-current baseline, in FIG. 15. Detection of DNA and maltodextrin required opposite voltage polarities for reasons discussed below. In addition to cis/trans nanopore selectivity for each analyte, the results in FIG. 16 show that detection of each analyte by the nanopore also required the correct applied voltage polarity. To successfully detect the biopolymer of interest thus required setting the nanopore to the correct cis configuration and the voltage to the analyte-specific voltage polarity.

In one embodiment, the biopolymer DNA (deoxyribonucleic acid) is the target of nanopore sensing. It is anionic and its charge allows for its direct electrophoresis-driven transport to and through the nanopore. DNA transport can also occur by diffusion and given a suitably charge-structured nanopore-solution interface, by electroosmosis of the solvent that may counter or reinforce electrophoretic transport of the DNA. The voltage polarity needed to detect DNA in these experiments is consistent with transport in the direction of electrophoretic motion, as is generally the case for nanopore DNA sensing. Discrete single-molecule blockages appearing as spikes in the upper trace of FIG. 3 were isolated by a thresholding against the temporally local average current. A reduced and unsteady baseline current is common in DNA sensing using unfunctionalized $SiN_x$ nanopores. It is generally ascribed to "sticking" of the DNA to the nanopore surface, and a plethora of surface chemical approaches have been developed to prevent such sticking. While 4-(propargyloxy)azobenzene coating did not completely prevent such sticking, the azobenzene backbone allows for flexibility in tuning substituents to chemically tune this behavior. The most impressive outcome of these DNA sensing experiments is that the photochromic pore can detect DNA and have its responsivity to DNA photoswitched.

Complex carbohydrates are a much less common analyte class than DNA for nanopore sensing, but are tremendously important and targeted in embodiments of the invention. Their much greater structural and compositional diversity result in complexity that challenges conventional analysis and has motivated high-profile calls for new tools. In an information storage sense, complex carbohydrates offer 120 possible naturally occurring monomers versus DNA's pre-epigenetic 4, meaning that carbohydrates provide the potential for an order of magnitude more density for information storage than DNA. Even in just an electrokinetic sense, the carbohydrate maltodextrin, for example, is the antithesis of DNA: it is neutral and therefore nonresponsive to electrophoresis. In the current state of the art, nanopore sensing is generally skewed towards electrophoresis because of the lack of a technology to reliably sense neutral molecules, so the disclosed successful detection of this neutral biopolymer—and by a photochromic nanopore—broadened the scope and reach of nanopore sensing. Maltodextrin was detected at only a single voltage polarity and at rates higher than would be expected by diffusion, consistent with electroosmotic detection. The successful detection of maltodextrin according to an embodiment of the present invention thus points to the presence of a charged nanopore surface as required for electroosmosis. The voltage polarity—opposite to that of electrophoresis for anionic DNA—indicates a negative surface charge. This charge sign would be displayed on an incompletely covered $SiN_x$ surface that would be terminated with $—O^-$ and $—NH_2$ at the sensing pH range.

Maltodextrin produced clear and distinct current blockages on a steady baseline when the nanopore was in the cis configuration. These events are not suggestive of untoward interactions between the maltodextrin and the photochromic nanopore. The magnitude of the blockages relative to the open pore current, and the temporal characteristics of the blockages are not dissimilar to those detected using conventional $SiN_x$ nanopores. This maltodextrin sensing data demonstrates that the nanopore sensing performance is not inherently compromised by the surface coating, but in fact compares well to an unmodified pore.

The nanopore functionalized according to principles of the invention was nonresponsive to DNA at the voltage polarity where it is responsive to maltodextrin because electroosmotic driving force is insufficient under the given sensing conditions to overcome the opposing electrophoretic driving force. Electroosmotic flow can be moderated by electrolyte salt concentration, providing an independent variable in addition to the wavelength and voltage polarity discussed here for tuning the nanopore responsivity (see Laohakunakorn N et al., (2015). Nano Lett, 15(1):695-702). The broad similarity of conductance versus pH curves for cis and trans configurations suggests that the trans configuration is not nonresponsive to the neutral maltodextrin because of a change in its surface charge. Rather, it suggests that the configurational dependence of the nanopore selectivity is dependent upon the physical size of the pore and possible effects of wetting differences of the coating. The lack of signal from either molecule by the trans nanopore is consistent with a lack of translocation through the nanopore suggesting that the pore can be employed as a photo-controlled delivery system in a different aspect of the invention as well. The responsivity of the photochromic nanopore, however, can be set by more than the illumination wavelength, i.e., the coating configuration. In the responsive cis configuration, the selectivity for one biopolymer versus the other is determined by the voltage polarity. In a mixture of two such biopolymers such as a polynucleotide (e.g., DNA) and a polysaccharide (e.g., maltodextrin), therefore, it is possible to select and detect a preferred class by the polarity of the applied voltage. Accordingly, in a separate aspect of the invention, multiplexed detection using the same photochromic nanopore is provided by adjusting one or more of the following variables: voltage polarity applied; cis-vs. trans-configuration in the coating as related to the pore size as determined optically or thermally; ionic conductance across the nanopore (i.e., nanopore conductance) and related parameters including pore-voltage gradient, the charge distribution and hydrophilicity of the pore surface, the ionic (or, electrolyte) concentration and the pH value of the solvent.

EXAMPLES

In a series of nanopore experiments conducted according to various embodiments of the invention, commercially obtained 4-(2-hydroxyethyl)-1-piperazineethanesulfonic acid (HEPES) potassium salt (H0527, ≥99.5% (titration)), potassium chloride (60130, puriss. p. a., ≥99.5% (AT)), potassium hydroxide (306568, 99.99%), hydrochloric acid (320331, ACS reagents, 37%), and acetonitrile (34998, ≥99.9) were used without further purification. Anhydrous ethanol (111000200, 100%) was purchased commercially and used without further purification.

Electrolyte solutions were prepared using Type I water (SYNSVHFUS, ~18 MΩ·cm resistivity) and passed through a vacuum filter system (S2GPU10RE, 0.22 μm pore polyethersulfone filter membrane. The electrolyte solutions were buffered with 10 mM HEPES and adjusted to pH 7 by adding concentrated HCl and KOH solutions dropwise as needed. All other aqueous solutions used in the examples were sourced from the type I water filter. Depending on the actual purpose and molecules involved, the sample solutions used in embodiments of the invention could include an aqueous solution, a polar solvent (e.g., an alcohol), a non-polar solvent (e.g., hexane or toluene), and/or an organic solvent.

Nanopore Fabrication

Isolated nanopores were formed by controlled dielectric breakdown. A 15=2 nm-thick low-pressure chemical vapor deposition (LPCVD) silicon nitride ($SiN_x$) membrane supported on 200 μm-thick commercially purchased silicon frames. Approximately, ~10 V was applied across the free-standing $SiN_x$ membrane immersed in 1 M KCl buffered to pH 7 in 10 mM HEPES. The resulting nanopore was characterized by its conductance which was calculated by a linear fit to its Ohmic current-voltage curve from −200 to 200 mV. Nanopore conductance measurements were made at an acquisition rate of 10 kHz using a 1 kHz Bessel filter. Current versus time measurements were collected over 10 to 20 minute periods with an acquisition rate of 100 kHz and 10 kHz Bessel filter.

Nanopore Photohydrosilylation

A small amount (~5 to 10 mg) of the azo switch in all trans configuration (confirmed by NMR) was moved to a 12 mL borosilicate glass sample vial. A minimum of acetonitrile was used to dissolve the solid. A membrane chip with freshly formed $SiN_x$ nanopore was rinsed with water, then ethanol, and then taken out of the polytetrafluoroethylene (PTFE) housing before being mounted in a custom aluminum reaction chamber, covered with the azobenzene solution and irradiated under a mercury UV lamp for at least 3 hours. The chip was then rinsed in ethanol and placed back into the PTFE fluid cell. The fluid cell was then filled with ethanol, water, and then the 1 M KCl electrolyte solution buffered at pH 7 (10 mM HEPES). The nanopore conductance was then measured and this measurement was labelled "initial."

Nanopore Photoswitching

Switching was achieved by irradiating the membrane with either white or 365 nm UV light to convert the azobenzene to its trans or cis configuration, respectively. The membrane was rinsed in its polytetrafluoroethylene (PTFE) holder by exchanging the electrolyte with water and then ethanol before removing it from the holder and placing it in the aluminum reaction chamber. The membrane was then covered with acetonitrile and irradiated under the relevant light source while shielded from ambient light. After desired irradiation time, the membrane was remounted and characterized by conductance in the PTFE holder as described above.

For UV-Vis experiments, HEPES potassium salt (H0527, ≥99.5% (titration)) was purchased and used without further purification. Potassium chloride (BP366-500, >99%), hydrochloric acid (A144-212, Certified ACS Plus, 36.5 to 38.0%), and acetonitrile (A998-4, ≥99.9%) was purchased and used without further purification. Aqueous solutions were prepared using Type I water (~18 MΩ·cm resistivity) and passed through a vacuum filter system using a 0.22 μm pore polyethersulfone filter membrane. The electrolyte solutions were buffered with mM HEPES and adjusted to pH 7 by adding concentrated HCl and KOH solutions dropwise as needed. Samples were irradiated with white light, 275 nm wavelength LED light, 365 nm wavelength LED or 430 nm wavelength LED light.

Procedure for Synthesis of 4-(propargyloxy)azobenzene

Samples of 4-azophenol (1.982 g, 10 mmol), potassium carbonate (6.910 g, 50 mmol, eq.), and anhydrous acetone (120 mL) were added to a flask and stirred for 30 minutes at room temperature under argon. Then, a solution of propargyl bromide (3.79 mL, 50 mmol, eq.) in acetone (16.2 mL) was added dropwise to the reaction mixture. The reaction was left to stir for 33 hours under argon. Upon completion of the reaction, the solvent was removed under reduced pressure and the product was obtained by column chromatography (9:1 hexanes:diethyl ether to 4:1 hexanes:diethyl ether) as an orange solid (1.289 g, 5.45 mmol, 54.5%). $^1$H NMR (CDCl3, 400 MHz) 7.94 (d, 2H), 7.88 (d, 2H), 7.51 (t, 2H), 7.45 (t, 1H), 7.10 (d, 1H), 4.78 (d, 2H), 2.57 (t, 1H).

The invention, thus conceived, is susceptible of numerous modifications and variations, all of which are within the scope of the appended claims. Moreover, all the details may be substituted by other, technically equivalent elements.

In practice the materials employed, provided they are compatible with the specific use, and the contingent dimensions and shapes, may be any according to requirements and to the state of the art.

Where technical features mentioned in any claim are followed by reference signs, such reference signs have been inserted for the sole purpose of increasing the intelligibility of the claims and accordingly such reference signs do not have any limiting effect on the interpretation of each element identified by way of example by such reference signs.

All publications and patent literature described herein are incorporated by reference in entirety to the extent permitted by applicable laws and regulations.

We claim:

1. A re-configurable translocation device capable of translocating a sample and distinguishing molecule types contained therein, the device comprising a cell that comprises:

(a) a source reservoir capable of holding a source solution and configured to be in electrical communication with an electrical source outside the cell, (b) a target reservoir capable of holding a target solution and configured to be in electrical communication with the electrical source outside the cell, and (c) a silicon-based membrane disposed between the source reservoir and the target reservoir, the membrane having at least one interior surface defining a nanopore having an average diameter between about 1 nm and about 100 nm, wherein the nanopore fully penetrates the membrane allowing passage of molecules between the source reservoir and the target reservoir, and wherein the interior surface defining the nanopore has been functionalized with at least one functional group comprising a photo-isomerizable compound, wherein the photo-isomerizable compound on the nanopore surface is responsive to either visible or ultraviolet light or both with at least one configurational change that alters the steric properties of the photo-isomerizable compound and effects distinguishing one molecule type from another based on a detectable change in electroosmotic or electrophoretic transport of the sample, thereby re-configures the nanopore, and wherein the detectable change comprises a change in pore conductance in connection with the passage of a molecule type through the nanopore; and wherein, when an electrical potential is applied between the electrical source outside the cell and both the source reservoir and the target reservoir, measurements of electrical signals between the source reservoir and the target reservoir can be made, thereby providing distinguishing information on different molecule types that pass between the source reservoir and the target reservoir.

2. The translocation device of claim 1 wherein electrolyte salt concentration in the source or target solution is varied to alter electroosmotic flow through the nanopore.

3. The translocation device of claim 1 wherein a valve is disposed between the target reservoir and the membrane.

4. A method of separating molecule types in a solution contained in the source reservoir of the translocation device of claim 3, comprising the sequential steps of:

(a) configuring the nanopore by subjecting the nanopore surface to an initial radiation of visible, ultra-violet light, or thermal energy, (b) applying a first electrical potential between the source reservoir and the target reservoir;

(c) operating the device for a first time period sufficient to translocate a first molecule type from the source reservoir into the target reservoir;

(d) preventing the first molecule type from passing back into the source reservoir through the valve and removing or otherwise isolating the first molecule type;

(e) optionally re-configuring the photo-isomerizable compound on the interior surface of the nanopore by subjecting the nanopore surface to radiation of visible, ultra-violet light or thermal energy;

(f) applying a second electrical potential between the source reservoir and the target reservoir; and (g) operating the device for a second time period sufficient to translocate a second and different molecule type from the source reservoir into the target reservoir.

5. A method of claim 4, wherein step (e) further comprises adjusting at least one of the parameters selected from the group consisting of pore conductance, voltage polarity applied, the charge distribution or characteristics of the pore surface, hydrophilicity of the pore surface, ionic-solvent-composition, and ionic-solvent-pH value.

6. The translocation device of claim 1 wherein any reservoir is removable.

7. The translocation device of claim 1 wherein the nanopore is capable of distinguishing between two molecule types in an ionic fluid by altering the ratio or direction of electroosmotic transport to electrophoretic transport through the nanopore.

8. The translocation device of claim 1 wherein the nanopore has of an average diameter between about 1 nm and about 20 nm.

9. The translocation device of claim 1 wherein the interior surface of the membrane defines two or more nanopores where the sizes of at least two nanopores vary.

10. The translocation device of claim 1 wherein the membrane is made from silicon nitride.

11. The translocation device of claim 1 wherein the photo-isomerizable compound comprises an azobenzene or an azobenzene derivative.

12. The translocation device of claim 1 wherein the distinguishing is made through resistive-pulse sensing.

13. The translocation device of claim 1 wherein the photo-isomerizable compound comprises a photochromic molecule selected from the group consisting of spiropyrans, hydrazones, donor-acceptor Stenhouse adducts, stilbenes, azobenzene, azobenzene derivatives, diarylethenes and diarylethene derivatives, and dithienylethenes and dithienylethene derivatives.

14. The translocation device of claim 1 wherein the membrane comprises a material selected from the group consisting of a polymer, an MXene, a transition metal dichalcogenide, silicon, silicon oxide, silicon nitride, graphene, molybdenum disulfide and hexagonal boron nitride.

15. The translocation device of claim 1, wherein the photo-isomerizable compound forms a monolayer on the nanopore surface with a thickness between 0.1 nm and 25 nm±5% or less.

16. The translocation device of claim 1, wherein the diameter of the pore is changed by a factor between 0 and approximately twice of length of the fully extended photo-switched molecule when the photoswitched molecule is changed between its available photo-isomers.

17. The translocation device of claim 1, wherein said one or more molecule types are each selected from the group consisting of oligo- or polynucleotides, oligo- or polypeptides, oligo- or polysaccharides, polymers, small molecules and mixtures thereof.

18. The translocation device of claim 17, wherein said one or more molecule types are each selected from the group consisting of DNA molecules, RNA molecules, neutral carbohydrates, charged carbohydrates, complex carbohydrates, proteins, lipids, sugars, starch, cellulose, collagen, and combinations thereof.

19. The translocation device of claim 18, wherein said complex carbohydrate is maltodextrin.

20. The translocation device of claim 17, wherein said photo-regulated nanopore may be tuned to either be responsive to sensing DNA or a complex carbohydrate biopolymer or unresponsive to sensing DNA or a complex carbohydrate biopolymer.

21. A method for manufacturing a photo-regulated nanopore sensor comprising the steps of:

conducting controlled dielectric breakdown of a silicon nitride membrane until at least one nanopore having an average diameter between about 1 nm and about 100 nm is formed across the membrane; and functionalizing an interior surface of said nanopore by photohydrosilyation of an azobenzene to the silicon nitride membrane until the azobenzene forms a monolayer covering substantially all of the nanopore surface.

22. The method for manufacturing a photo-regulated nanopore sensor according to claim 21, wherein said azobenzene is 4-(propargyloxy) azobenzene.

23. The method for manufacturing a photo-regulated nanopore sensor according to claim 21, wherein the thickness of the silicon nitride membrane is between 20 to 100 nm±5% after the photohydrosilyation step.

24. The method for manufacturing a photo-regulated nanopore sensor according to claim 21, wherein the thickness of the silicon nitride membrane is between 1 to 20 nm±5% after the photohydrosilyation step.

* * * * *